Figure 3:
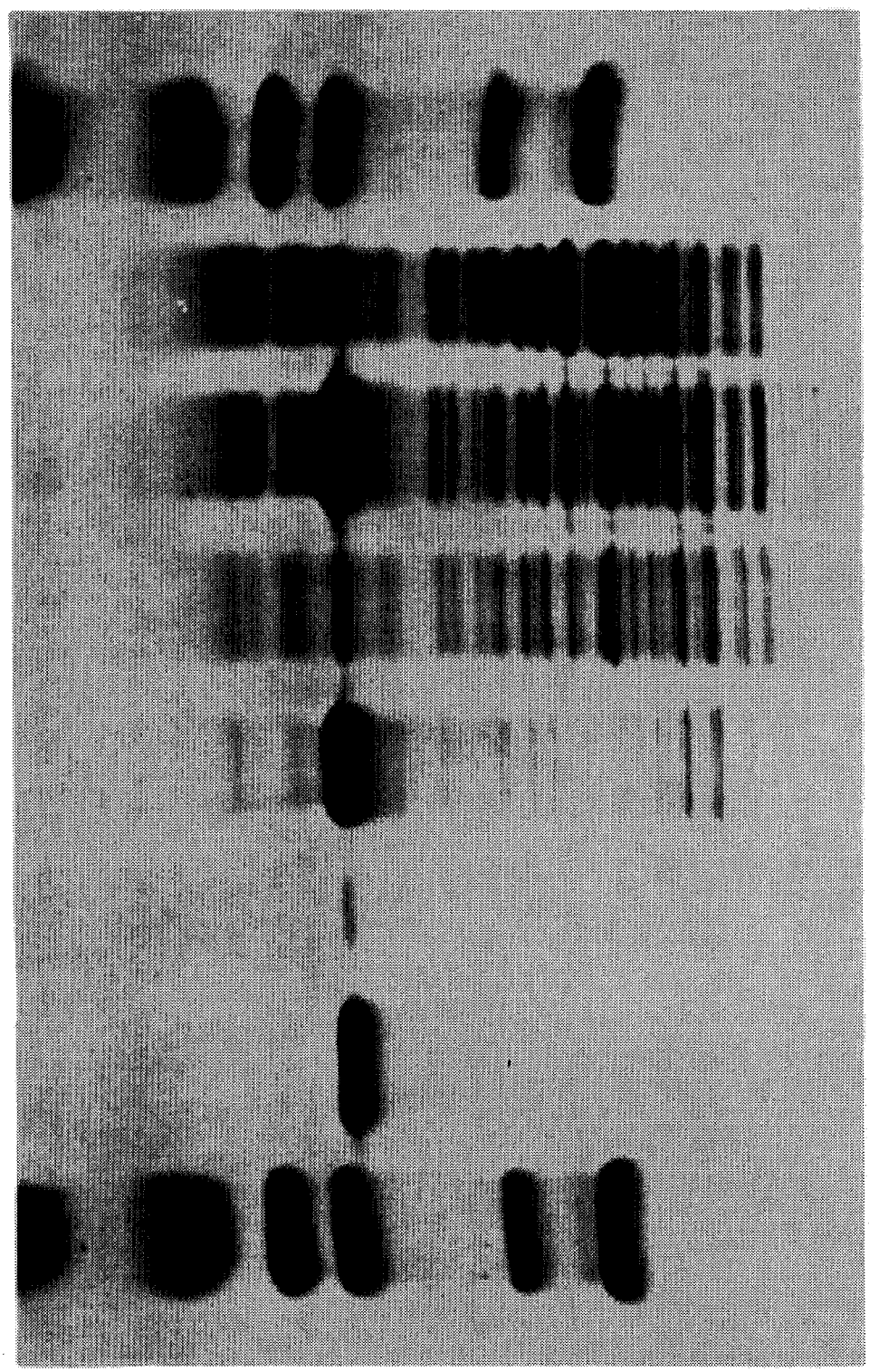

United States Patent [19]
Shoseyov et al.

[11] Patent Number: 5,496,934
[45] Date of Patent: Mar. 5, 1996

[54] NUCLEIC ACIDS ENCODING A CELLULOSE BINDING DOMAIN

[75] Inventors: Oded Shoseyov, Karmey Yosef; Itai Shpiegl, Rehovot, both of Israel; Marc A. Goldstein; Roy H. Doi, both of Davis, Calif.

[73] Assignees: Yissum Research Development Company of the Hebrew University of Jerusalem, Israel; The Regents of the University of California, Calif.

[21] Appl. No.: 48,164

[22] Filed: Apr. 14, 1993

[51] Int. Cl.$^6$ ............................ C07H 21/04; C12N 15/31
[52] U.S. Cl. .................... 536/23.7; 536/23.1; 536/24.33; 435/320.1; 435/252.3
[58] Field of Search ................................ 536/23.7, 23.1, 536/24.33; 435/320.1, 252.3

[56] References Cited

U.S. PATENT DOCUMENTS 5,137,819  8/1992  Kilburn et al. ........................ 435/179
5,229,501  7/1993  Keifer et al. ........................... 530/399

OTHER PUBLICATIONS

Bowie et al. 1990. Science 247: 1306–1310.
Watson et al. 1987. *Molecular Biology of The Gene*, Fourth Ed., p. 313.
Jauris et al. 1990. Mol. Gen. Genet. 223:258–267.
Poole et al. 1992. FEMS Microbiol. Lett. 99:181–6.
Nilsson et al., "Immobilization and purification of enzymes with staphylococcal protein A gene fusion vectors," *EMBO J.* 4(4):1075–1080 (1985).
Mehra et al., "Efficient mapping of protein antigenic determinants," *Proc. Natl. Acad. Sci. USA* 83: 7013–7017 (1986).
Shinnick, Thomas M., "The 65–Kilodalton Antigen of *Mycobacterium tuberculosis*," *J. of Bacteriology* 169(3):1080–1088 (1987).
Cabib, Enrico, "Chitinase from *Serratia marcescens*," *Methods in Enzymology* 161:460–462 (1988).
van Enden et al., "Cloning of the mycobacterial epitope recognized by T lymphocytes in adjuvant arthritis," *Nature* 331:171–173 (1988).
Shinnick et al., "The *Mycobacterium tuberculosis* 65–Kilodalton Antigen Is a Heat Shock Protein Which Corresponds to Common Antigen and to the *Escherichia coli* GroEL Protein," *Infection and Immunity* 56(2):446–451 (1988).
Hemmingsen et al., "Homologous plant and bacterial proteins chaperone oligomeric protein assembly," *Nature* 333:330–334 (1988).
Greenwood et al., "Fusion to an endoglucanase allows alkaline phosphatase to bind to cellulose," *EBS Letters* 244(1):127–131 (1989).
Jindal et al., "Primary Structure of a Human Mitochondrial Protein Homologous to the Bacterial and Plant Chaperonins and to the 65–Kilodalton Mycobacterial Antigen," *Mol. and Cell. Biol.* 9(5):2279–2283 (1989).
Picketts et al., 'Molecular Cloning of a Chinese Hamster Mitochondrial Protein Related to the "Chaperonin" Family of Bacterial and Plant Proteins,' *J. Biol. Chem.* 264: 12001–12008 (1989).
Ellis, John, "The molecular chaperone concept," *Seminars in Cell Biology* 1:1–9 (1990).
Billingham et al., "A Mycobacterial 65–kD Heat Shock Protein Induces Antigen–Specific Suppression of Adjuvant Arthritis, But Is Not Itself Arthritogenic," *J. Exp. Med.* 171:339–344 (1990).
Elias et al., "Induction and therapy of autoimmune diabetes in the non–obese diabetic (NOD/Lt) mouse by a 65–kDa heat shock protein," *Proc. Natl. Acad. Sci. USA* 87:1576–1580 (1990).
Shoseyov et al., "Essential 170–kDa subunit for degradation of crystalline cellulose by *Clostridium cellulovorans* cellulase," *Proc. Natl. Acad. Sci. USA* 87:2192–2195 (1990).
Shoseyov et al., "Immobilized Endo–β–glucosidase Enriches Flavor of Wine and Passion Fruit Juice," *JAFCU* 38(6):1387–1390 (1990).
Venner et al., "Nucleotide sequence of rat hsp60 (chaperonin, GroEL homolog) cDNA," *Nuc. Acids Res.* 18(17):5309 (1990).
Klyosov, Anatole A., "Trends in Biochemistry and Enzymology of Cellulose Degradation," *Biochemistry* 29(47):10577–10585 (1990).
van Eden, Willem, "Heat–Shock Proteins as Immunogenic Bacterial Antigens with the Potential to Induce and Regulate Autoimmune Arthritis," *Immunological Reviews* 121:5–28 (1991).
Shoseyov et al., "Primary sequence analysis of *Clostridium cellulovorans* cellulose binding protein A," *Proc. Natl. Acad. Sci. USA* 89:3483–3487 (1992).
Hermann et al., "Synovial fluid–derived Yersinia–reactive T cells responding to human 65–kDa heat-shock protein and heat-stressed antigen–presenting cells," *Eur. J. Immunol.* 21:2139–2143 (1991).
Din et al., "Non–Hydrolytic Disruption of Cellulose Fibres by the Binding Domain of a Bacterial Cellulase," *Bio/Technology* 9:1096–1099 (1991).

*Primary Examiner*—Marianne P. Allen
*Assistant Examiner*—Elizabeth C. Kemmerer
*Attorney, Agent, or Firm*—Pennie & Edmonds

[57] ABSTRACT

A cellulose binding domain (CBD) having a high affinity for crystalline cellulose and chitin is disclosed, along with methods for the molecular cloning and recombinant production thereof. Fusion products comprising the CBD and a second protein are likewise described. A wide range of applications are contemplated for both the CBD and the fusion products, including drug delivery, affinity separations, and diagnostic techniques.

11 Claims, 13 Drawing Sheets

```
            10          20          30          40          50
             .           .           .           .           .
GCA GCG ACA TCA TCA ATG TCA GTT GAA TTT TAC AAC TCT AAC AAA TCA GCA CAA
CGT CGC TGT AGT AGT TAC AGT CAA CTT AAA ATG TTG AGA TTG TTT AGT CGT GTT
Ala Ala Thr Ser Ser Met Ser Val Glu Phe Tyr Asn Ser Asn Lys Ser Ala Gln>
                             10

60          70          80          90         100
         .           .           .           .           .
ACA AAC TCA ATT ACA CCA ATA ATC AAA ATT ACT AAC ACA TCT GAC AGT GAT TTA
TGT TTG AGT TAA TGT GGT TAT TAG TTT TAA TGA TTG TGT AGA CTG TCA CTA AAT
Thr Asn Ser Ile Thr Pro Ile Ile Lys Ile Thr Asn Thr Ser Asp Ser Asp Leu>
         20                                  30

110         120         130         140         150         160
  .           .           .           .           .           .
AAT TTA AAT GAC GTA AAA GTT AGA TAT TAT TAC ACA AGT GAT GGT ACA CAA GGA
TTA AAT TTA CTG CAT TTT CAA TCT ATA ATA ATG TGT TCA CTA CCA TGT GTT CCT
Asn Leu Asn Asp Val Lys Val Arg Tyr Tyr Tyr Thr Ser Asp Gly Thr Gln Gly>
             40                                      50

170         180         190         200         210
         .           .           .           .           .
CAA ACT TTC TGG TGT GAC CAT GCT GGT GCA TTA TTA GGA AAT AGC TAT GTT GAT
GTT TGA AAG ACC ACA CTG GTA CGA CCA CGT AAT AAT CCT TTA TCG ATA CAA CTA
Gln Thr Phe Trp Cys Asp His Ala Gly Ala Leu Leu Gly Asn Ser Tyr Val Asp>
                         60                                      70

220         230         240         250         260         270
        .           .           .           .           .           .
AAC ACT AGC AAA GTG ACA GCA AAC TTC GTT AAA GAA ACA GCA AGC CCA ACA TCA
TTG TGA TCG TTT CAC TGT CGT TTG AAG CAA TTT CTT TGT CGT TCG GGT TGT AGT
Asn Thr Ser Lys Val Thr Ala Asn Phe Val Lys Glu Thr Ala Ser Pro Thr Ser>
                             80                                      90
```

FIG.1A

```
              280           290           300           310           320
               .             .             .             .             .
ACC TAT GAT ACA TAT GTT GAA TTT GGA TTT GCA AGC GGA CGA GCT ACT CTT AAA
TGG ATA CTA TGT ATA CAA CTT AAA CCT AAA CGT TCG CCT GCT CGA TGA GAA TTT
Thr Tyr Asp Thr Tyr Val Glu Phe Gly Phe Ala Ser Gly Arg Ala Thr Leu Lys>
                                         100

330           340           350           360           370
       .             .             .             .             .
AAA GGA CAA TTT ATA ACT ATT CAA GGA AGA ATA ACA AAA TCA GAC TGG TCA AAC
TTT CCT GTT AAA TAT TGA TAA GTT CCT TCT TAT TGT TTT AGT CTG ACC AGT TTG
Lys Gly Gln Phe Ile Thr Ile Gln Gly Arg Ile Thr Lys Ser Asp Trp Ser Asn>
             110                         120

380           390           400           410           420           430
   .             .             .             .             .             .
TAC ACT CAA ACA AAT GAC TAT TCA TTT GAT GCA AGT AGT TCA ACA CCA GTT GTA
ATG TGA GTT TGT TTA CTG ATA AGT AAA CTA CGT TCA TCA AGT TGT GGT CAA CAT
Tyr Thr Gln Thr Asn Asp Tyr Ser Phe Asp Ala Ser Ser Thr Pro Val Val>
                 130                         140

440           450           460           470           480
       .             .             .             .             .
AAT CCA AAA GTT ACA GGA TAT ATA GGT GGA GCT AAA GTA CTT GGT ACA GCA CCA
TTA GGT TTT CAA TGT CCT ATA TAT CCA CCT CGA TTT CAT GAA CCA TGT CGT GGT
Asn Pro Lys Val Thr Gly Tyr Ile Gly Gly Ala Lys Val Leu Gly Thr Ala Pro>
                 150                                             160
```

FIG.1B

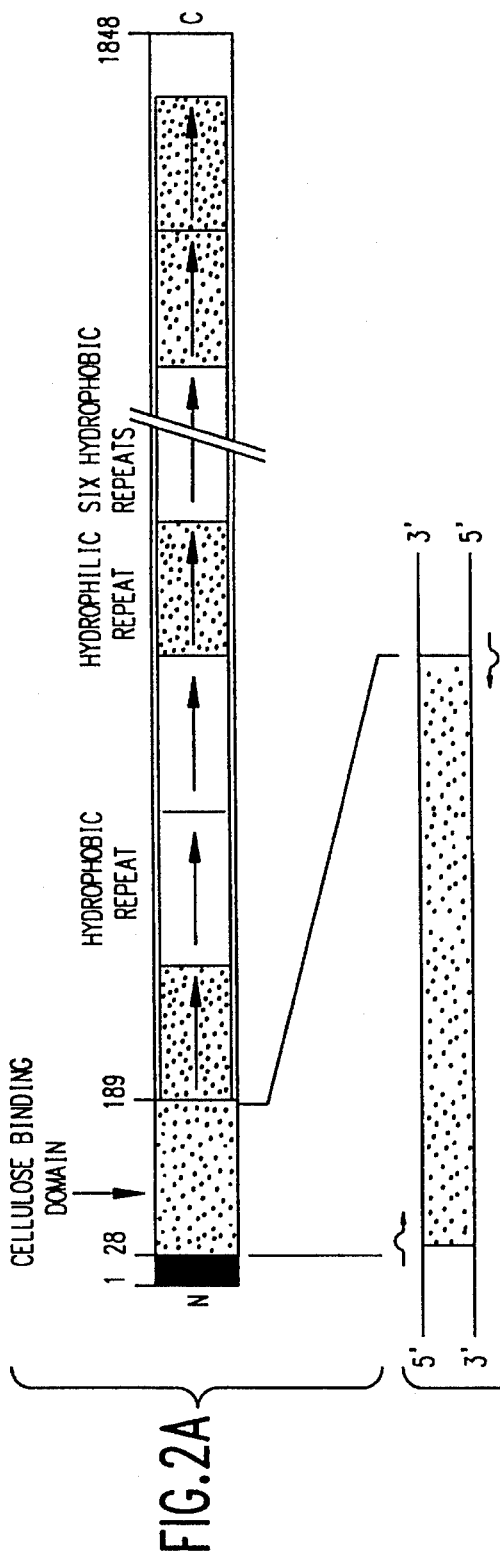
FIG.2A
FIG.2B
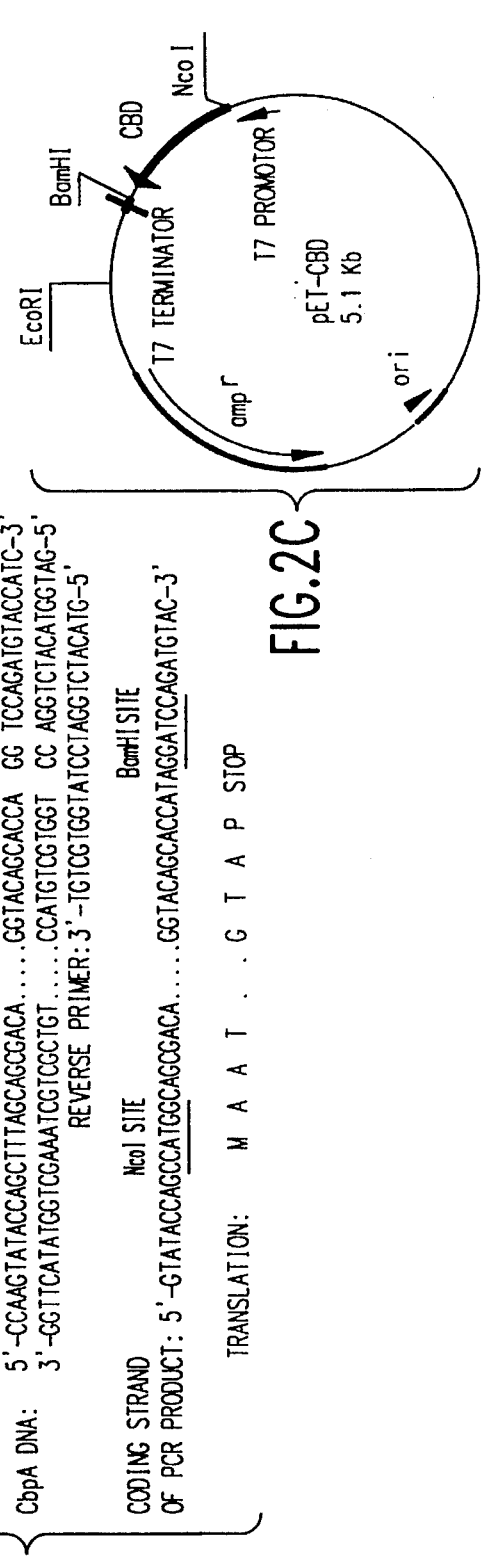
FIG.2C

| SUBSTRATE: | OBSERVED $K_d$ (in μM) | OBSERVED $PC_{max}$ (in μmoles CBD/g) |
|---|---|---|
| AVICEL PH101 | 1.1 ± 0.3 | 1.4 ± 0.3 |
| SIGMACELL 20 | 1.1 | 1.2 |
| SIGMACELL 50 | 1.4 | 1.7 |
| SIGMACELL 100 | 1.3 | 0.5 |
| MICROGRANULAR CELLULOSE | 1.0 | 0.4 |
| FIBROUS CELLULOSE | 1.4 | 0.2 |
| COTTON | 0.8 | 6.4 |
| CELLULON | 1.2 | 5.3 |
| XYLAN | — | 0 |
| SEPHADEX G-75 | — | 0 |
| NIGERAN | — | 0 |
| CHITIN | 1.0 | 1.6 |
| AVICEL PH101 | | |
| +CMC (4mg/ml) | 1.1 | 1.1 |
| +CELLOBIOSE (4mg/ml) | 1.0 | 1.5 |

FIG. 9

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 486 base pairs
( B ) TYPE: nucleic acid
( C ) STRANDEDNESS: double
( D ) TOPOLOGY: unknown ( i i ) MOLECULE TYPE: DNA ( i x ) FEATURE:
( A ) NAME/KEY: CDS
( B ) LOCATION: 1..486

( x i ) SEQUENCE DESCRIPTION: SEQ ID NO:1:

```
GCA  GCG  ACA  TCA  TCA  ATG  TCA  GTT  GAA  TTT  TAC  AAC  TCT  AAC  AAA  TCA        48
Ala  Ala  Thr  Ser  Ser  Met  Ser  Val  Glu  Phe  Tyr  Asn  Ser  Asn  Lys  Ser
 1              5                        10                       15

GCA  CAA  ACA  AAC  TCA  ATT  ACA  CCA  ATA  ATC  AAA  ATT  ACT  AAC  ACA  TCT        96
Ala  Gln  Thr  Asn  Ser  Ile  Thr  Pro  Ile  Ile  Lys  Ile  Thr  Asn  Thr  Ser
             20                        25                       30

GAC  AGT  GAT  TTA  AAT  TTA  AAT  GAC  GTA  AAA  GTT  AGA  TAT  TAT  TAC  ACA       144
Asp  Ser  Asp  Leu  Asn  Leu  Asn  Asp  Val  Lys  Val  Arg  Tyr  Tyr  Tyr  Thr
         35                        40                       45

AGT  GAT  GGT  ACA  CAA  GGA  CAA  ACT  TTC  TGG  TGT  GAC  CAT  GCT  GGT  GCA       192
Ser  Asp  Gly  Thr  Gln  Gly  Gln  Thr  Phe  Trp  Cys  Asp  His  Ala  Gly  Ala
     50                        55                       60

TTA  TTA  GGA  AAT  AGC  TAT  GTT  GAT  AAC  ACT  AGC  AAA  GTG  ACA  GCA  AAC       240
Leu  Leu  Gly  Asn  Ser  Tyr  Val  Asp  Asn  Thr  Ser  Lys  Val  Thr  Ala  Asn
 65                        70                       75                       80

TTC  GTT  AAA  GAA  ACA  GCA  AGC  CCA  ACA  TCA  ACC  TAT  GAT  ACA  TAT  GTT       288
Phe  Val  Lys  Glu  Thr  Ala  Ser  Pro  Thr  Ser  Thr  Tyr  Asp  Thr  Tyr  Val
                         85                       90                       95

GAA  TTT  GGA  TTT  GCA  AGC  GGA  GCA  GCT  ACT  CTT  AAA  AAA  GGA  CAA  TTT       336
Glu  Phe  Gly  Phe  Ala  Ser  Gly  Ala  Ala  Thr  Leu  Lys  Lys  Gly  Gln  Phe
                    100                      105                      110

ATA  ACT  ATT  CAA  GGA  AGA  ATA  ACA  AAA  TCA  GAC  TGG  TCA  AAC  TAC  ACT       384
Ile  Thr  Ile  Gln  Gly  Arg  Ile  Thr  Lys  Ser  Asp  Trp  Ser  Asn  Tyr  Thr
               115                      120                      125
```

| | | | | | | | | | | | | | | | |
|---|---|---|---|---|---|---|---|---|---|---|---|---|---|---|---|
| CAA | ACA | AAT | GAC | TAT | TCA | TTT | GAT | GCA | AGT | AGT | TCA | ACA | CCA | GTT | GTA | 432
| Gln | Thr | Asn | Asp | Tyr | Ser | Phe | Asp | Ala | Ser | Ser | Ser | Thr | Pro | Val | Val |
| | 130 | | | | 135 | | | | | | 140 | | | | |
| AAT | CCA | AAA | GTT | ACA | GGA | TAT | ATA | GGT | GGA | GCT | AAA | GTA | CTT | GGT | ACA | 480
| Asn | Pro | Lys | Val | Thr | Gly | Tyr | Ile | Gly | Gly | Ala | Lys | Val | Leu | Gly | Thr |
| 145 | | | | 150 | | | | | 155 | | | | | 160 | |
| GCA | CCA | | | | | | | | | | | | | | | 486
| Ala | Pro | | | | | | | | | | | | | | |

( 2 ) INFORMATION FOR SEQ ID NO:2:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ala | Ala | Thr | Ser | Ser | Met | Ser | Val | Glu | Phe | Tyr | Asn | Ser | Asn | Lys | Ser |
| 1 | | | | 5 | | | | | 10 | | | | | 15 |
| Ala | Gln | Thr | Asn | Ser | Ile | Thr | Pro | Ile | Ile | Lys | Ile | Thr | Asn | Thr | Ser |
| | | | 20 | | | | | 25 | | | | | 30 | | |
| Asp | Ser | Asp | Leu | Asn | Leu | Asn | Asp | Val | Lys | Val | Arg | Tyr | Tyr | Tyr | Thr |
| | | 35 | | | | | 40 | | | | | 45 | | | |
| Ser | Asp | Gly | Thr | Gln | Gly | Gln | Thr | Phe | Trp | Cys | Asp | His | Ala | Gly | Ala |
| | 50 | | | | | 55 | | | | | 60 | | | | |
| Leu | Leu | Gly | Asn | Ser | Tyr | Val | Asp | Asn | Thr | Ser | Lys | Val | Thr | Ala | Asn |
| 65 | | | | | 70 | | | | | 75 | | | | | 80 |
| Phe | Val | Lys | Glu | Thr | Ala | Ser | Pro | Thr | Ser | Thr | Tyr | Asp | Thr | Tyr | Val |
| | | | | 85 | | | | | 90 | | | | | 95 | |
| Glu | Phe | Gly | Phe | Ala | Ser | Gly | Ala | Ala | Thr | Leu | Lys | Lys | Gly | Gln | Phe |
| | | | 100 | | | | | 105 | | | | | 110 | | |
| Ile | Thr | Ile | Gln | Gly | Arg | Ile | Thr | Lys | Ser | Asp | Trp | Ser | Asn | Tyr | Thr |
| | | 115 | | | | | 120 | | | | | 125 | | | |
| Gln | Thr | Asn | Asp | Tyr | Ser | Phe | Asp | Ala | Ser | Ser | Ser | Thr | Pro | Val | Val |
| | 130 | | | | | 135 | | | | | 140 | | | | |
| Asn | Pro | Lys | Val | Thr | Gly | Tyr | Ile | Gly | Gly | Ala | Lys | Val | Leu | Gly | Thr |
| 145 | | | | | 150 | | | | | 155 | | | | | 160 |
| Ala | Pro | | | | | | | | | | | | | | |

( 2 ) INFORMATION FOR SEQ ID NO:3:

( i ) SEQUENCE CHARACTERISTICS:
        ( A ) LENGTH: 486 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:3:

| | | | | | |
|---|---|---|---|---|---|
| TGGTGCTGTA | CCAAGTACTT | TAGCTCCACC | TATATATCCT | GTAACTTTTG | GATTTACAAC | 60
| TGGTGTTGAA | CTACTTGCAT | CAAATGAATA | GTCATTTGTT | TGAGTGTAGT | TTGACCAGTC | 120
| TGATTTTGTT | ATTCTTCCTT | GAATAGTTAT | AAATTGTCCT | TTTTTAAGAG | TAGCTGCTCC | 180
| GCTTGCAAAT | CCAAATTCAA | CATATGTATC | ATAGGTTGAT | GTTGGGCTTG | CTGTTTCTTT | 240
| AACGAAGTTT | GCTGTCACTT | TGCTAGTGTT | ATCAACATAG | CTATTTCCTA | ATAATGCACC | 300
| AGCATGGTCA | CACCAGAAAG | TTTGTCCTTG | TGTACCATCA | CTTGTGTAAT | AATATCTAAC | 360

TTTTACGTCA TTTAAATTTA AATCACTGTC AGATGTGTTA GTAATTTTGA TTATTGGTGT 420

AATTGAGTTT GTTTGTGCTG ATTTGTTAGA GTTGTAAAAT TCAACTGACA TTGATGATGT 480

CGCTGC 486

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:4:

GTATACCAGC CATGGCAGCG 20

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:5:

CCAAGTATAC CAGCTTTAGC AGCGACA 27

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:6:

GGTACAGCAC CAGGTCCAGA TGTACCATC 29

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:7:

GATGGTACAT CTGGACCTGG TGCTGTACC 29

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: unknown ( i i ) MOLECULE TYPE: DNA ( x i ) SEQUENCE DESCRIPTION: SEQ ID NO:8:

```
TGTCGCTGCT AAAGCTGGTA TACTTGG                                                                   27
```

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:9:

```
GTACATCTGG ATCCTATGGT GCTGT                                                                     25
```

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 12..23

( x i ) SEQUENCE DESCRIPTION: SEQ ID NO:10:

```
GTATACCAGC C ATG GCA GCG ACA                                                                    23
             Met Ala Ala Thr
              1
```

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Ala Ala Thr
 1
```

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA ( i x ) FEATURE:
        ( A ) NAME/KEY: CDS
        ( B ) LOCATION: 1..15

( x i ) SEQUENCE DESCRIPTION: SEQ ID NO:12:

```
GGT ACA GCA CCA TAGGATCCAG ATGTAC                                                               28
Gly Thr Ala Pro
 1           5
```

( 2 ) INFORMATION FOR SEQ ID NO:13:

( i ) SEQUENCE CHARACTERISTICS:
        ( A ) LENGTH: 4 amino acids
        ( B ) TYPE: amino acid (D) TOPOLOGY: linear (i i) MOLECULE TYPE: protein (x i) SEQUENCE DESCRIPTION: SEQ ID NO:13:

Gly Thr Ala Pro
 1

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (i i) MOLECULE TYPE: DNA (x i) SEQUENCE DESCRIPTION: SEQ ID NO:14:

GGGGGAATTC CATGGCAGCG ACAT　　　　　　　　　　　　　　　　　　　24

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (i i) MOLECULE TYPE: DNA (x i) SEQUENCE DESCRIPTION: SEQ ID NO:15:

GGGGGGATCC TATGGTGCT　　　　　　　　　　　　　　　　　　　　　　19

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (i i) MOLECULE TYPE: DNA (x i) SEQUENCE DESCRIPTION: SEQ ID NO:16:

ACGGTACCAC TTCGGTTACC CACAGTC　　　　　　　　　　　　　　　　27

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: unknown
        (D) TOPOLOGY: unknown (i i) MOLECULE TYPE: DNA (x i) SEQUENCE DESCRIPTION: SEQ ID NO:17:

GGGGATCCTA CATGCCACCT CCCATTAG　　　　　　　　　　　　　　　28

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (i i) MOLECULE TYPE: DNA ( x i ) SEQUENCE DESCRIPTION: SEQ ID NO:18:

GTACATCTGG ATCCTATGGT ACCGT                                              2 5

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:19:

AGCCATGGCG GCCCAGC                                                       1 7

( 2 ) INFORMATION FOR SEQ ID NO:20:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:20:

GGGGTACCAA CAGTTTGTGC GGCC                                               2 4

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA ( x i ) SEQUENCE DESCRIPTION: SEQ ID NO:21:

GGGCCATGGC AGGTACCTCA TCA                                                2 3

NUCLEIC ACIDS ENCODING A CELLULOSE BINDING DOMAIN

The Government has rights in this invention pursuant to Contract No. DE-FG03-92ER20069 awarded by the Department of Energy.

TABLE OF CONTENTS
1. INTRODUCTION
2. BACKGROUND OF THE INVENTION
    2.1 Immobilization of Proteins
    2.2 Cellulose
    2.3 Cellulase
    2.4 Heat Shock Protein (HSP)
3. SUMMARY OF THE INVENTION
4. DESCRIPTION OF THE FIGURES
5. DETAILED DESCRIPTION OF THE INVENTION
    DEFINITIONS
6. EXAMPLE: EXPERIMENTAL PROCEDURE FOR CLONING OF THE PUTATIVE CELLULOSE BINDING DOMAIN
    6.1 Materials and Methods
        6.1.1 Bacterial Strains and Plasmids
        6.1.2 Materials
        6.1.3 Cloning of Putative Cellulose Binding Domains
        6.1.4 Expression of CBD
7. EXAMPLE: PURIFICATION OF CBD PROTEIN
    7.1 Preparation of CBD Protein
        7.1.1 Purification of CBD Protein
        7.1.2 Determination of the CBD-Cellulose Dissociation Constant and the Cellulose Binding Capacity
        7.1.3 Determination of Binding to Other Polysaccharides
    7.2 Results
        7.2.1 Purification of the CBD for Binding Analyses
        7.2.2 Time course of the Binding of the CBD to Cellulose
        7.2.3 Analysis of the CBD-Cellulose Binding Affinity and Binding Capacity
        7.2.4 Binding Site Competition
        7.2.5 Effect of pH on the Dissociation Constant
        7.2.6 Binding of the CBD to Other Polysaccharides
    7.3 Results
8. CONSTRUCTION OF CBD-ProtA GENE AND ITS EXPRESSION IN E. COLI
    8.1 Material and Methods
        8.1.1 Enzymes and Chemicals
        8.1.2 Plasmids and Bacteria
        8.1.3 Cloning of CBD-ProtA
        8.1.4 Expression and purification of CBD-ProtA
        8.1.5 Binding Analysis of CBD-ProtA
        8.1.6 Results
9. CLONING OF CBD-HSP FUSION PROTEIN
10. CONSTRUCTION OF $NH_2$-$V_H$-$V_L$-CBD-$CO_2$
CLAIMS
ABSTRACT

1. INTRODUCTION

The present invention relates to a cellulose binding domain (CBD) that binds to water-insoluble forms of cellulose and chitin, including crystalline forms, with a remarkably high affinity and in a reversible manner. The CBD of the present invention, which has been isolated and which is substantially free of other proteins with which the CBD is naturally associated, finds use, for example, in the bio-immobilization of a wide variety of substances, especially biologically active molecules, to cellulose. Fusion products comprising the CBD and a second protein of interest are also disclosed, including applications in methods for their preparation. Such fusion proteins enjoy a wide range of useful applications, including applications in separation, purification and diagnostic methods.

2. BACKGROUND OF THE INVENTION

2.1 Immobilization of Proteins

Immobilization of chemical substances, including biologically active proteins, is of great importance to industry. Various methods of immobilization have been developed in recent years. However, most of these methods require chemical modification of a solid matrix. Typically, these modifications require the covalent attachment of a ligand to the matrix resulting, in many cases, in loss of activity of the ligand as well as the inclusion of toxic organic compounds that must be removed before the matrix can be used in medicine or food processing. A typical example of a widely used product is Protein A-Sepharose. This highly expensive product is used for the purification of IgG by affinity chromatography, as well as for many diagnostic protocols.

The use of chimeric proteins, i.e., those that contain a functional domain (catalytic or otherwise) together with a binding domain, is relatively new but has already proven to be very useful, especially in protein purification methods. For example, the glutathione S-transferase gene fusion system is designed to express a gene of interest fused to the C-terminal of glutathione S-transferase. The recombinant protein is purified by affinity chromatography using glutathione-Sepharose column.

Another example of a chimeric protein having a functional domain and a binding domain is the Protein-A gene fusion vector which has been designed to permit a high level of expression of fusion proteins in both *E. coli* and *Staphylococcus aureus* cells. B. Nilsson, et al. (1985) *EMBO J.* 4(4):1075–1080. The IgG binding domain of Protein A provides a rapid purification method of the fusion protein using IgG-Sepharose columns. Similar systems have been developed based on beta-galactosidase fusion proteins purified on IPTG-Sepharose or metal chelate chromatography or histidine hexamer fusion proteins using Ni-resin columns. All these methods use expensive matrices such as Sepharose, acrylic beads, or glass beads that require costly chemical modifications and in many cases, the use of highly toxic compounds. Cellulose, on the other hand, has excellent physical properties and is inexpensive, thus providing an attractive solid matrix for protein immobilization.

2.2 Cellulose

Cellulose has been very useful for immobilization of endo-beta-glucosidase, an enzyme that is used for wine and fruit juice treatments (Shoseyov et al. *J. Agric. Food Chem.* 38:1387–1390 [1990].). However, immobilization requires the chemical modification of the cellulose and results in a fluffy compressible material that is not suitable for applications involving packed columns.

A cellulose substrate, to which a ligand could be bound without resort to chemical modification (e.g., "bioimmobilized"), would possess the advantage that the resulting solid matrix is natural and non-toxic (having required no "dirty chemical modifications"). It would be further advantageous if the resulting solid matrix retained its physical properties, as well as its relatively low price. At present, cellulose prices are 100–500 fold lower than those of glutathione-Sepharose and IPTG-Sepharose, making cellulose an attractive, inexpensive matrix that can be used safely in food and pharmaceutical industries.

Recently, Greenwood et. al. (*FEBS Lett.* 224(1): 127–131 [1989].) fused the cellulose binding region of *Cellulomonas fimi* endoglucanase to the enzyme alkaline phosphatase. The recombinant fusion protein retained both its phosphatase activity and the ability to bind to cellulose. See, also U.S. Pat. No. 5,137,819 granted to Kilburn et al., incorporated by reference herein.

Unfortunately, the *Cellulomonas fimi* cellulose binding region exhibits a relatively low affinity to cellulose. For instance, more than 30% of the fusion protein is washed off by 50 mM Tris-HCl (pH 7.5) in 0.5M NaCl. A second disadvantage of the *C. fimi* cellulose binding region is that the cellulose fibers are disrupted upon binding to the *C. fimi* binding region (Din et al., *Bio/Technology* 9: 1096–1098 [1991]). Therefore, even though the *C. fimi* cellulose binding region may not exhibit direct cellulase activity, this disruption of the fibers of the cellulose substrate, which is tantamount to a physical change in the morphology of the solid matrix, is equally problematic and undesirable. (See, further, the discussion in Section 7.3, below.)

2.3 Cellulase

Many cellulases and other hydrolytic enzymes, such as chitinases, have high affinities for their substrates (Shoseyov, et al., *PNAS* USA vol., 87, pg. 2192–2195 [1990]; Cabib, *Methods Enzymol.* vol. 161, pp. 460–462 [1988]). It has previously been shown that strong binding between crystalline cellulose and the cellulase is directly related to that cellulase's ability to degrade crystalline cellulose (Klyosov, *Biochemistry* vol. 29, pp. 10577–10585 [1990]), whereas strong binding is not necessary for that cellulase's ability to degrade amorphous cellulose.

Shoseyov, et al., (*PNAS* USA vol. 87, pp. 2192–2195 [1990]) report purification of the cellulase "complex" from *Clostridium cellulovorans*. This cellulase "complex" exhibits cellulase activity against crystalline cellulose, as well as carboxymethylcellulose, and is a large protein complex consisting of several different polypeptides. It has been found that a large (ca. 200 kD) major cellulose binding protein (CpbA), with no apparent enzyme activity, must participate with the catalytic enzyme in order for the catalytic enzyme to breakdown crystalline cellulose. However, no such participation by the CpbA is necessary for the enzymatic degradation of amorphous cellulose. Shoseyov, et al., (PNAS USA, vol. 89, pp. 3483–3487 [1992]) report the cloning and DNA sequencing of the gene for CpbA, including a description of four separate "putative" cellulose binding domains within the CpbA.

2.4 Heat Shock Protein (HSP)

Heat shock proteins (HSP) are induced in prokaryotic and Eukaryotic species under various conditions of stress. The HSP's are grouped into families of homologous proteins based on their molecular masses.

The 60 kD HSP (hsp 60) family, which retained a uniquely high level of sequence conservation during evaluation is a focus of interest as a potential antigen in autoimmune diseases. W. Van Eden (1991) *Immunol. Rev.* 121:1; W. Van Eden, Thole R. Van der Zee, A. Noordzij, J. D. A. Van Einbden, E. J. Hensen, and I. R. Cohen (1988) Nature 331:171; M. B. J. Billingham S. Carney, R. Bulter, and M. J. Colston (1990) *J. Exp. Med.* 171:339.

There is experimental evidence that response to hsp 60 is subject to regulatory T cell control. It has been suggested that T cell reactivity is directed, at least partly, against the mammalian endogenous HSP. B. Herman et al. (1991) *Eur. J. Immunol.* 21:2139.

The genes coding for hsp 60 protein family have been cloned and sequenced from a number of different species including *Mycobacterium tuberculosis, Micobacterium leprae, Mycobacterium bovis* BCG, *E. coli*, chinese hamster rat mouse and human cells. V. Mera et al. (1986) *Proc. Nat. Acad. Sci. USA* 83:7013; S. Jindal et al. (1989) *Mol. Cell. Biol.* 9:2279; O. J. Picketts et al. (1989) *J. Biol. Chem.* 264:12001; T. M. Shinnick (1987) *J. Bacteriol.* 169:1080; T. M. Shinnick et al. (1988) *Infect. Immun.* 56:446; T. J. Venner and R. S. Gupta (1990) *Nucl. Acids. Res.* 18:5309.

Immune response to Mycobacterial and human hsp 60 has been implicated in the development of autoimmune diabetes in human and animal models.

Besides being an immunodominant antigen, the hsp 60 family of proteins in various systems has been shown to perform a "molecular chaperone" role in the proper folding of newly synthesized polypeptide chains and, in some cases, their assembly into oligomeric protein complexes. S. M. Hemmingsen et al. *Nature* 333:330; R. J. Ellis (1990) *Sem. Cell Biol.* 1:1–9.

In a model system in mice for insulin dependent diabetes mellitus (IDDM)—T lymphocytes responding to the hsp 60 antigen are detectable at the onset of insulitis and it is likely that these T lymphocytes can also recognize the Beta cell hsp 65 cross reactive antigen. D. Elias et al. (1990) *Proc. Nat. Acad. Sci. USA* 87:1576–1580.

Thus, there remains an unfulfilled need to discover a cellulose binding protein that exhibits a high but reversible affinity for cellulose, particularly crystalline cellulose, but which manifests neither cellulase activity nor an ability to disrupt the fibers of the crystalline cellulose substrate (i.e., does not exhibit an "amorphogenic" effect).

3. SUMMARY OF THE INVENTION

The inventors describe herein the identification, molecular cloning and cellulose binding characteristics of a novel cellulose binding domain (CBD) protein. Also, disclosed is the construction of an expression system for the production of a fusion product comprising the CBD and a second protein of interest.

The invention relates to the discovery that the CBD is able to function independently of the other proteins or polypeptides with which it is naturally associated. Moreover, it has been discovered unexpectedly that the CBD has a high affinity for crystalline cellulose and chitin, having a $K_d$ ranging from about 1.5 to about 0.8, preferably ranging from about 1.4 to about 0.8. In particular, with various samples of crystalline cellulose, the CBD exhibits a $K_d$ of about 1.2 or less. The CBD can be further characterized in that it possesses virtually no cellulase activity and, quite surprisingly, the CBD exhibits no morphology-altering characteristics (i.e., no amorphogenic effects). It has also been discovered that CBD-fusion products comprising CBD and a second protein retain the avid binding capacity of the CBD to cellulose.

The invention is also related to the discovery that the CBD demonstrates absolute binding to cellulose over a wide range of pH and under different buffering conditions, that large quantities of CBD bind to crystalline cellulose, and that exposure to water fails to release CBD from cellulose. In stark contrast, the major CpbA protein, as well as the binding region from C. fimi, are readily dissociated from cellulose on exposure to water. Indeed, exposure to denaturing solutions, such as 6M guanidine-HCl, 6M urea or nonionic surfactants, is required to release the CBD from cellulose. Thus, the CBD protein functions and behaves quite independently of the rest of the other proteins with which it is naturally associated in its binding to cellulose.

Thus, the present invention provides an isolated CBD protein capable of binding cellulose with high affinity and which is substantially free of other proteins with which it is naturally associated.

In one embodiment of the present invention, a CBD protein comprises the amino acid sequence shown in FIG. 1. In another embodiment of the present invention, the CBD protein comprises an amino acid sequence having at least 70% sequence similarity, preferably 80% sequence similarity, to the amino acid sequence disclosed in FIG. 1. In another aspect of the present invention, a nucleic acid is contemplated having at least 60% sequence similarity, preferably 70–80% homology, to the nucleic acid sequence depicted in FIG. 1.

In yet another embodiment of the present invention, the CBD protein has a high binding affinity to cellulose. More preferably, the CBD of the present invention has a $K_d$ of about 1.1 or less, most preferably 1.0 or less.

In yet another embodiment, the present invention provides a CBD fusion protein comprised of a CBD protein capable of binding cellulose with high affinity and a second protein wherein, when said CBD protein is one which occurs in nature, said CBD protein is substantially free of other proteins with which it is naturally associated. In a particular embodiment of the present invention, the second protein is Protein A. In another embodiment of the present invention, the second protein is an HSP protein. In yet another embodiment of the present invention, the second protein fused to the CBD may be comprised of two or more polypeptide regions. For example, the CBD may be fused to the variable light chain ($V_L$) and the variable heavy chain ($V_H$) of an antibody or functional portions thereof.

A further embodiment of the present invention provides a method for the production of a CBD or a CBD fusion product. An exemplary procedure, which can be applied either to CBD alone or to a CBD fusion product, but which is recited herein for a CBD fusion product, may comprise the following steps: providing nucleic acid encoding the CBD fusion product wherein said CBD fusion product is comprised of a CBD and a second protein, said CBD being capable of binding cellulose or chitin with high affinity and being substantially free of other proteins with which it is naturally associated; transfecting a host cell with the nucleic acid or using an equivalent means for introducing the nucleic acid into the host cell; and (2) culturing the transformed host cell under conditions suitable for expression of the CBD fusion protein. In the above method, the second protein may be further comprised of an N-terminal amino acid and a C-terminal amino acid. Transfection of the host cell can be effected in a number of ways well known to those of ordinary skill in the art, including, but not limited to, electroporation, injection, calcium chloride precipitation and retroviral introduction. Furthermore, the nucleic acid can be either integrated with the genome of the hose cell or not.

In a further aspect of the present invention, a method of the purification of a CBD fusion product is provided comprising contacting a mixture comprising a recombinant CBD fusion product with an effective amount of cellulose under conditions suitable for the formation of an insoluble binding complex comprising cellulose and the recombinant fusion product; isolating the insoluble cellulose-CBD fusion product binding complex from the mixtures; and recovering the CBD fusion protein from the cellulose-CBD fusion product binding complex.

In a particular embodiment of the present invention, the method of purifying a CBD fusion protein of the present invention further comprises providing nucleic acid encoding a cleavage site upstream of the N-terminal amino acid of the second protein of the CBD fusion product.

In another embodiment of the present invention, the method for purifying a CBD fusion protein further comprises providing nucleic acid encoding a cleavage site downstream of the C-terminal amino acid of the second protein of the CBD fusion protein.

In yet another embodiment of the present invention the method for purifying a CBD fusion protein of the present invention further comprises providing nucleic acid encoding a first cleavage site upstream of the N-terminal amino acid of the second protein and a second cleavage site downstream of the C-terminal amino acid of the second protein of the CBD fusion protein.

Similarly, CBD is purified by contacting a mixture comprising CBD with an effective amount of cellulose. Isolation of the resulting insoluble CBD-cellulose binding complex followed by treatment of the binding complex with a releasing reagent provides the purified CBD.

Another aspect of the present invention provides an isolated nucleic acid encoding a CBD protein which is capable of binding cellulose with high affinity and which is substantially free of other nucleic acid with which it is naturally associated. An isolated nucleic acid encoding a protein of the present invention may be useful as a probe in screening cDNA or genomic libraries for sequences having homology to cbd gene.

In further embodiments, the present invention provides for a host cell comprised of nucleic acid encoding a CBD of the present invention.

An additional aspect of the present invention relates to a diagnostic kit for the detection of a substance of interest comprising: (a) a CBD fusion product comprising (i) a CBD capable of binding to cellulose with high affinity and substantially free of other proteins with which it is naturally associated, and (ii) a second protein capable binding a substance of interest; (b) a detectable label; and (c) cellulose. In such a diagnostic kit, the cellulose can be replaced by chitin. In specific embodiments of the present invention, the second protein of the CBD fusion product can be Protein A, HSP protein, HSP antibody, HSP-related protein, peptide or antigenic portion thereof. The term "peptide" is meant to include molecules comprising 2–20 amino acids. The CBD fusion product of the disclosed diagnostic kit may further comprise a ligand affinity bound to the second protein, such ligand capable of binding a substance of interest. By "ligand" is meant any molecule that is able to bind a second molecule by any non-covalent means. For example, a primary IgG can be affinity bound to Protein A fused to CBD. The IgG may then serve as a ligand for a particular protein, peptide or hormone.

In another aspect of the present invention, an immunoassay method of detecting the presence of a substance of interest in a test sample is disclosed comprising: (a) incubating a test sample, which may contain a substance of interest, with a sufficient amount of a CBD fusion product comprising (i) a CBD capable of binding to cellulose with high affinity and substantially free of other proteins with which it is naturally associated, and (ii) a second protein capable of binding the substance of interest, under conditions that allow for the binding of the substance of interest to the second protein of the CBD fusion product; (b) adding an amount of cellulose effective to bind the amount of the CBD fusion product used in step (a) to provide an insoluble cellulose-CBD fusion product binding complex; (c) separating the insoluble cellulose-CBD fusion product binding complex from unbound components; (d) incubating the insoluble cellulose-CBD fusion product binding complex with a sufficient amount of a detectable label, the label capable of binding to the substance of interest; and (e) separating the insoluble cellulose-CBD fusion product binding complex of step (d) from unbound components and determining the presence or absence of the label, to provide an indication of the presence or absence of the substance of interest in the test sample.

Another method is also disclosed for the detection of a substance of interest in a test sample comprising: (a) contacting a test sample, which may contain a substance of interest, with an insoluble matrix capable of immobilizing the substance of interest; (b) incubating the insoluble matrix with a sufficient amount of a CBD fusion product comprising (i) a CBD capable of binding to cellulose with high affinity and substantially free of other proteins with which it is naturally associated, and (ii) a second protein capable of binding the immobilized substance of interest, under conditions that allow for the binding of the immobilized substance of interest to the second protein of the CBD fusion product; (c) separating the insoluble matrix of step (b) from unbound components; (d) incubating the insoluble matrix of step (c) with a detectable label capable of binding the substance of interest or the CBD fusion product under conditions that allow for the binding of the label to the substance of interest or the CBD fusion product; and (e) separating the insoluble matrix of step (d) from unbound components and determining the presence or absence of the label, to provide an indication of the presence or absence of the substance of interest in the test sample.

This method may further comprise (i) contacting the insoluble matrix of step (c) with a sufficient amount of cellulose under conditions that allow for the binding of the cellulose to the CBD fusion product to form a cellulose-CBD fusion product binding complex, and (ii) separating the insoluble matrix of step (i) from unbound components, including unbound cellulose. This method can use a label that is capable of binding the substance of interest or the cellulose-CBD fusion protein binding complex, in particular, the cellulose of the cellulose-CBD fusion protein binding complex. The test sample may be a bodily fluid, including, but not limited to, blood, urine, semen, saliva, mucus, tears, vaginal secretions, and the like. As usual, the cellulose can be replaced by chitin. Also, the insoluble matrix may be an electrophoresis gel blot.

In a specific embodiment of the present invention, the method is designed for the detection of a protein or peptide; thus, the second protein of the CBD fusion product may be an antibody against the protein or peptide. The substance of interest may also comprise a biotinylated probe bound to a protein, peptide, hormone, nucleic acid or other probe-targetable molecule. In this case, the preferred second protein is streptavidin. Where the label includes an enzyme, the method further comprises adding a sufficient amount of a substrate for the enzyme, which substrate is converted by the enzyme to a detectable compound.

The assay may also be carried out in a competitive mode. Hence, the above-described method may be modified such that step (d) is performed by incubating the insoluble cellulose-CBD fusion product binding complex with a sufficient amount of a detectable label comprising a labeled substance of interest, the label capable of binding to any second protein of the CBD fusion product which remains unbound to the substance of interest, and in which step (e) is performed by separating the insoluble cellulose-CBD fusion product binding complex of step (d) from unbound components and comparing the signal observed from the test sample relative to the signal observed from a control sample.

In a preferred embodiment of the present invention, the CBD fusion product is included in a dip stick. Hence, it is also an object of the present invention to provide a dip stick useful in detecting a substance of interest in a test sample comprising a CBD fusion product, the CBD fusion product comprising (i) a CBD capable of binding to cellulose with high affinity and substantially free of other proteins with which it is naturally associated, and (ii) a second protein capable of binding a substance of interest. Preferably, the second protein is selected from the group consisting of Protein A, HSP protein, HSP antibody, cross-reactive HSP-related protein or peptide or an antigenic portion thereof, an enzyme, hormone, antigen, and antibody.

Likewise, it is also an object of the present invention to provide a signal amplification system comprising: (a) a first CBD fusion product comprising (i) a CBD capable of binding to cellulose with high affinity and substantially free of other proteins with which it is naturally associated, and (ii) a second protein capable of binding a chimeric probe, the probe further capable of binding a substance of interest; and (b) a second CBD fusion product comprising (i) a CBD capable of binding to cellulose with high affinity and substantially free of other proteins with which it is naturally associated, and (ii) an enzyme capable of acting on a substrate to produce a detectable compound.

In another embodiment, a signal amplification system is provided which comprises: (a) a CBD fusion product comprising (i) a CBD capable of binding to cellulose with high affinity and substantially free of other proteins with which it is naturally associated, and (ii) a second protein capable of binding a chimeric probe, the probe further capable of binding a substance of interest; and (b) labeled CBD, the CBD retaining its capacity to bind to cellulose with high affinity and substantially free of other proteins with which it is naturally associated.

These signal amplification systems may include the chimeric probe and may further include a cellulose matrix, preferably a pebble-milled cellulose.

Finally, it is a further object of the present invention to provide a drug delivery system comprising CBD associated with a drug, the CBD retaining its capacity to bind to cellulose with high affinity and substantially free of other proteins with which it is naturally associated. In such a drug delivery system, the drug is conjugated to the CBD either directly or through a linker moiety. Many methods of conjugation exist and are known in the art. For example, acyl activation agents exist, such as cyclohexylcarbodiimide, which can be used to form amide or ester bonds. Thus, a drug having a nucleophilic group, such as amino or hydroxy may be attached to the carboxy terminal end of CBD.

In one embodiment, the drug to be delivered is an antifungal agent. Preferred agents, include, but are not limited to, Amphotericin B, Nystatin, and Undecylenic Acid. The drug may generally be an imidazole, such as Clotrimazole. It is contemplated that such a drug delivery system can be incorporated into a composition that can be administered parenterally, orally, topically or by inhalation. In particular, routes of administration include, but are not limited to, intranasal, opthalmic or intravaginal. Furthermore, the composition may be in the form of a solid, gel, liquid or aerosol.

The drug delivery systems described herein are useful for the delivery of a drug to an infectious or disease-causing agent, such as a yeast or fungal agent whose cellular membrane contains a cellulosic or chitinic substance. Examples of such agents, include, but are not limited to, *Aspergillus fumigatus*, a member of the genus Candida or Monilia, or an epidermatocyte. By employing the drug delivery system of the present invention, it is anticipated that the dosages required for effective treatment of the disease or infection will be much reduced, thus, improving the effectiveness of the antifungal or antimycosal drugs, which are typically also quite toxic. It is hoped that side effects are, thus, also minimized or, even better, eliminated.

4. DESCRIPTION OF THE FIGURES

FIGS. 1A and 1B. Nucleotide (top, orig. [SEQ ID No: 1]; second line, complement [SEQ ID NO: 3]) and deduced amino acid sequence [SEQ ID NO: 2] of CBD.

FIG. 2. Preparation and cloning of the gene fragment encoding CBD.

A. Analysis of the primary structure of CbpA, which contains an N-terminus signal peptide, unique CBD region, 4 hydrophilic repeats (white arrows), and 8 hydrophobic repeats (black arrows).

B. PCR primer placement along the cbpA gene. Included for clarity are the primer sequences (Forward Primer [SEQ ID NO: 4]; Reverse Primer [SEQ ID NO: 9]) and the cbpA DNA sequence (5' to 3' [SEQ ID NOS: 5 and 6]; 3' to 5' [SEQ ID NOS: 7 and 8]) of the CBD flanking regions. The PCR product contains NcoI and BamHI sites [SEQ ID NOS: 10 and 12, respectively], underlined. Also note that the ATG start codon [SEQ ID NO: 17] for the gene fragment is located within the NcoI site, and the TAG stop [SEQ ID NO: 13] is adjacent to the BamHI site.

C. Schematic of pET-CBD, containing the CBD gene fragment cloned into the pET-8c vector. The vector contains the necessary transcriptional and translational signals for inducible CBD production.

FIG. 3. Expression and purification of the CBD protein.

Whole cell proteins from cells harboring pET-8c (lane 2), whole cell proteins from cells harboring pET-CBD (lane 3), cytosolic fraction from lysed pET-CBD cells (lane 4), Guanidine HCl-solubilized membrane/inclusion body fraction from lysed pET-CBD cells (lane 5), final PC buffer wash of AVICEL (microcrystalline cellulose) pellet (lane 6), and purified CBD protein (lane 7) were loaded on a 15% acrylamide gel. Each lane was loaded with 0.005% of the total protein of each fraction, except lane 6 which is a 10-fold concentrate. Prestained molecular mass markers (lanes 1,8) have mobilities of approximately 2.6, 5, 12.7, 18.1, 29, and 44 kDa.

Figure 4:
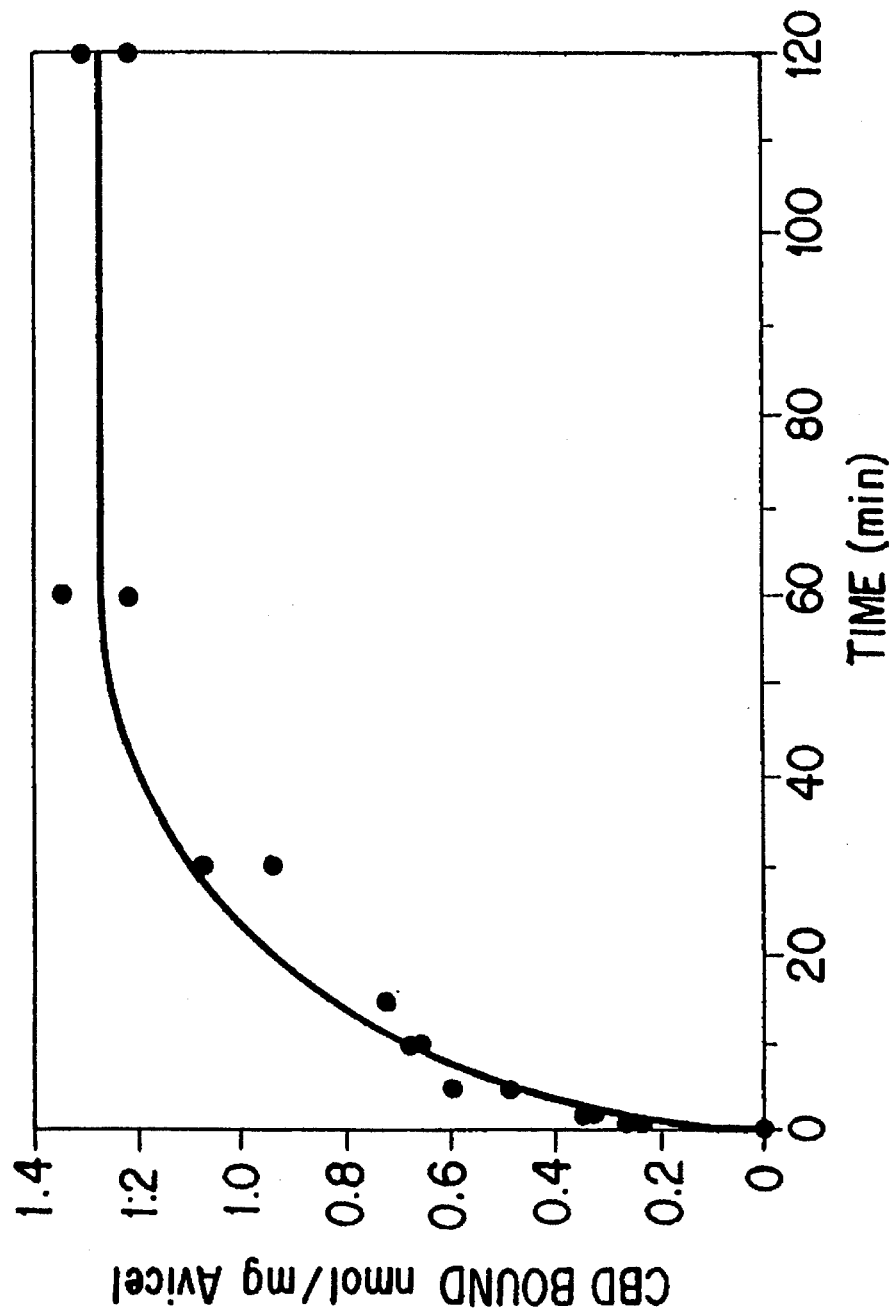

FIG. 4. Time course of CBD-AVICEL (microcrystalline cellulose) binding. CBD (2.0 μmol total protein) and AVICEL (microcrystalline cellulose) (1 mg/ml) were equilibrated as described in Section 7, below, except that a larger total volume was used to provide samples taken at various time points. Each time point sample was washed and assayed as described in Section 7. See, also, Table I of FIG. 9, below.

Figure 5B:
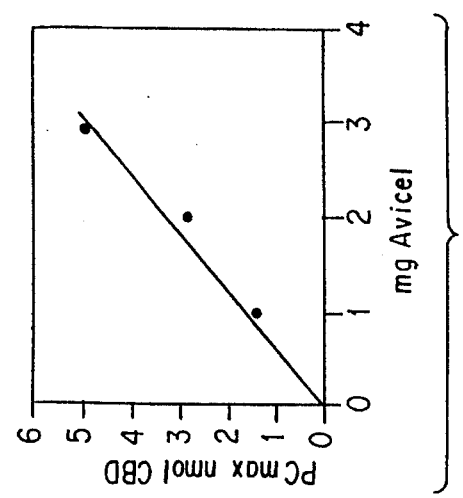
Figure 5A:
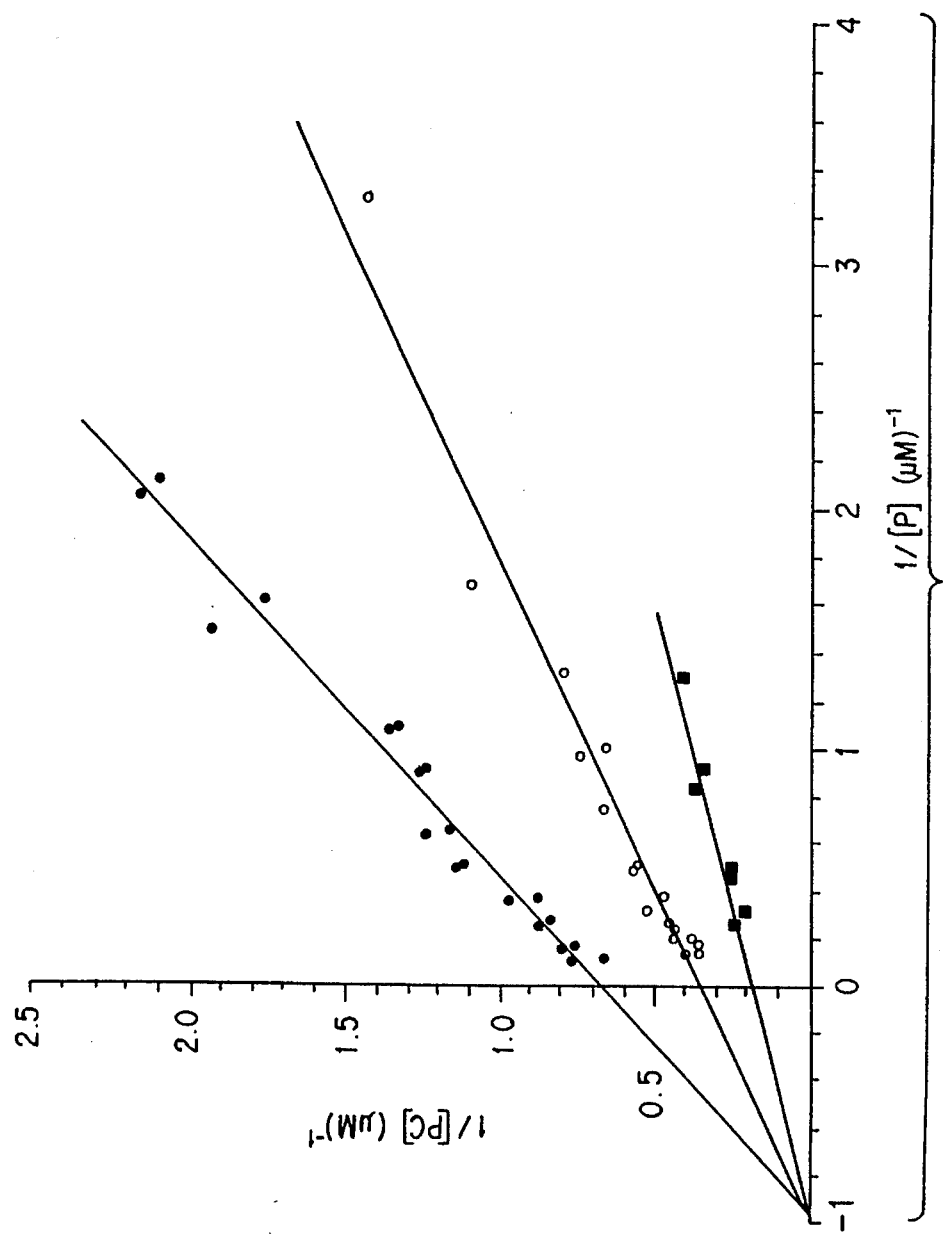

FIG. 5. Double reciprocal plot of CBD binding to AVICEL (microcrystalline cellulose) 0.5 mg AVICEL (microcrystalline cellulose) is represented by closed squares (B), 1 mg AVICEL (microcrystalline cellulose) by closed circles (J), and 2 mg by closed triangles (H). Inset: $PC_{max}$ versus the amount of AVICEL (microcrystalline cellulose) used. The assay volume was 1.0 ml.

Figure 6:
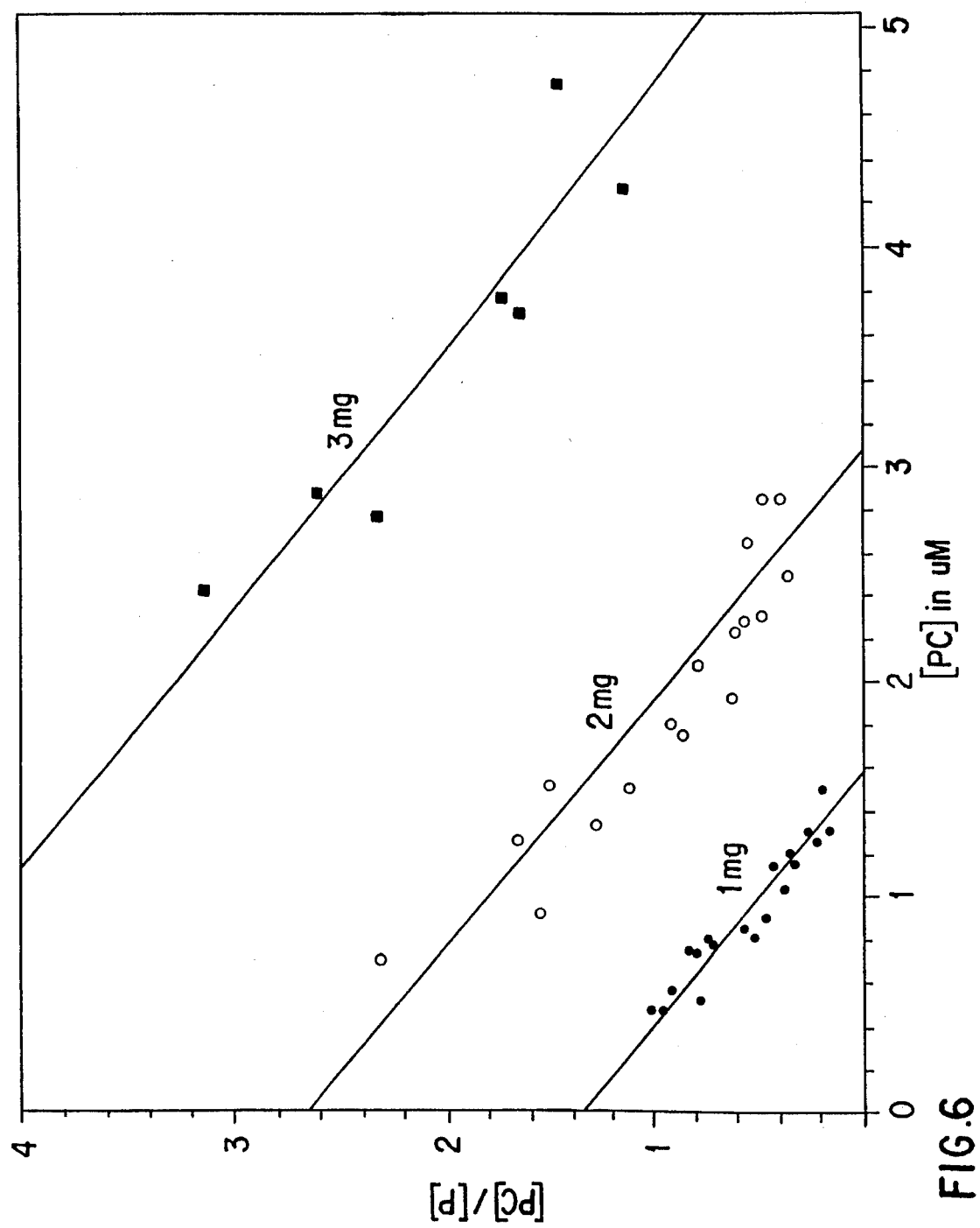

FIG. 6. Scatchard Plot CBD binding to AVICEL (microcrystalline cellulose). The [PC]/[P] vs. PC for 3 amounts of AVICEL (microcrystalline cellulose) are shown. The [PC]/[P] is expressed as a dimensionless ratio, and the [PC] is shown in μM. 1 mg AVICEL (microcrystalline cellulose) is represented by closed circles, 2 mg AVICEL (microcrystalline cellulose) by open circles, and 3 mg by closed squares.

Figure 7:
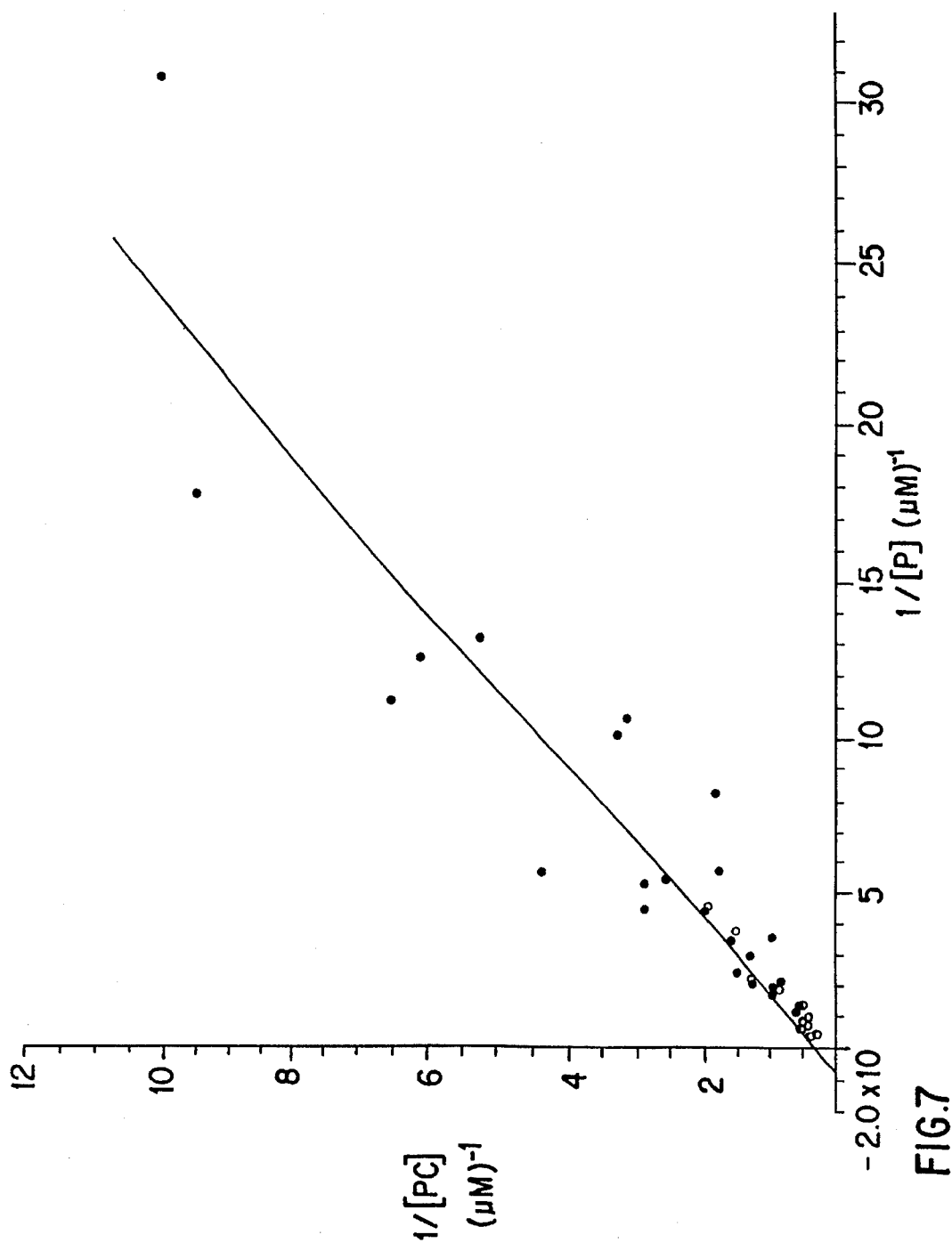

FIG. 7. Double reciprocal plot CBD binding to CELLULON (crystaline cellulose from Acetobacter Xylinum). The incubation mixture contained 0.5 mg CELLULON(crystaline cellulose from Acetobacter Xylinum) per ml. /

Figure 8:
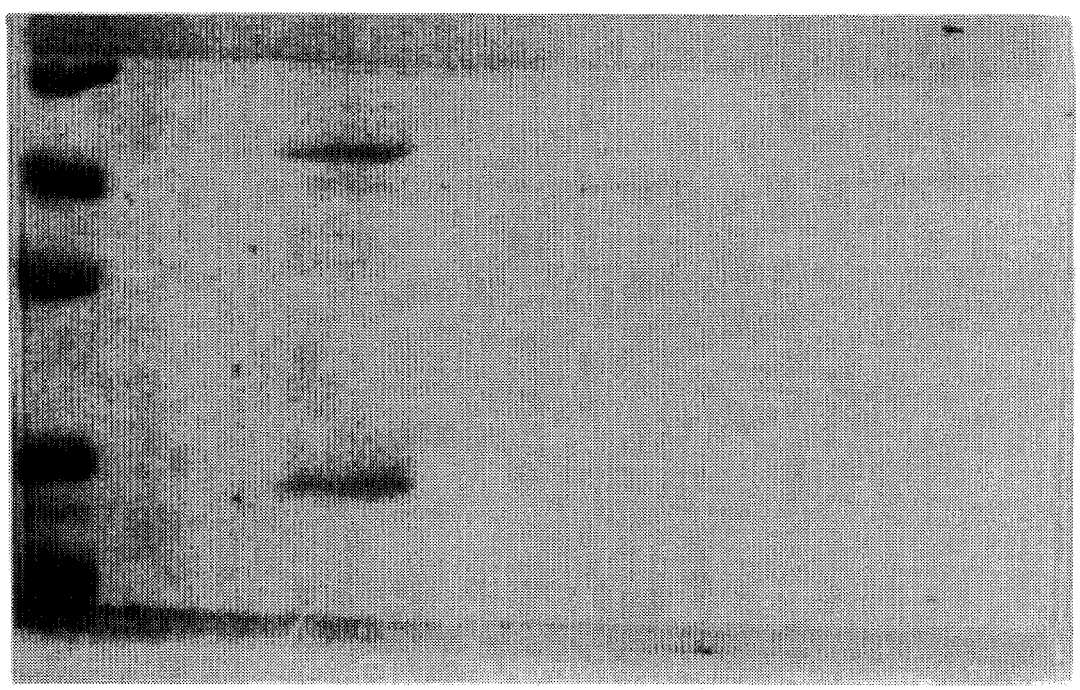

FIG. 8. CBD-ProtA fusion protein binds both Cellulose and IgG. 1M Acetic acid selectively releases CBD-ProtA:IgG "bond", but not the CBD-ProtA:cellulose "bond".

FIG. 9. Adsorption of CBD protein to insoluble substrates.

Figure 10:
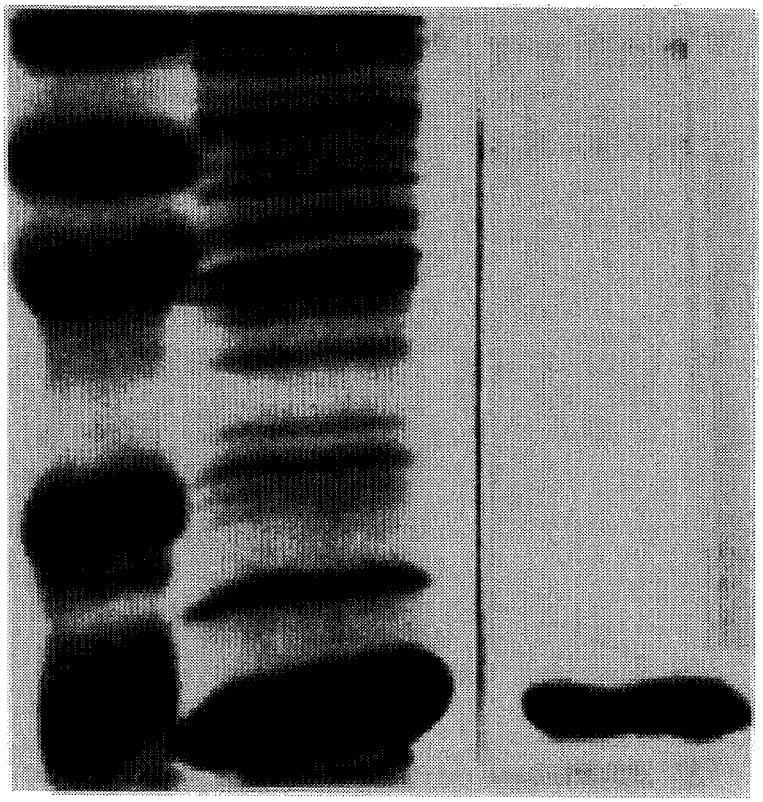

FIG. 10. Overexpression and purification of CBD.

Figure 11:
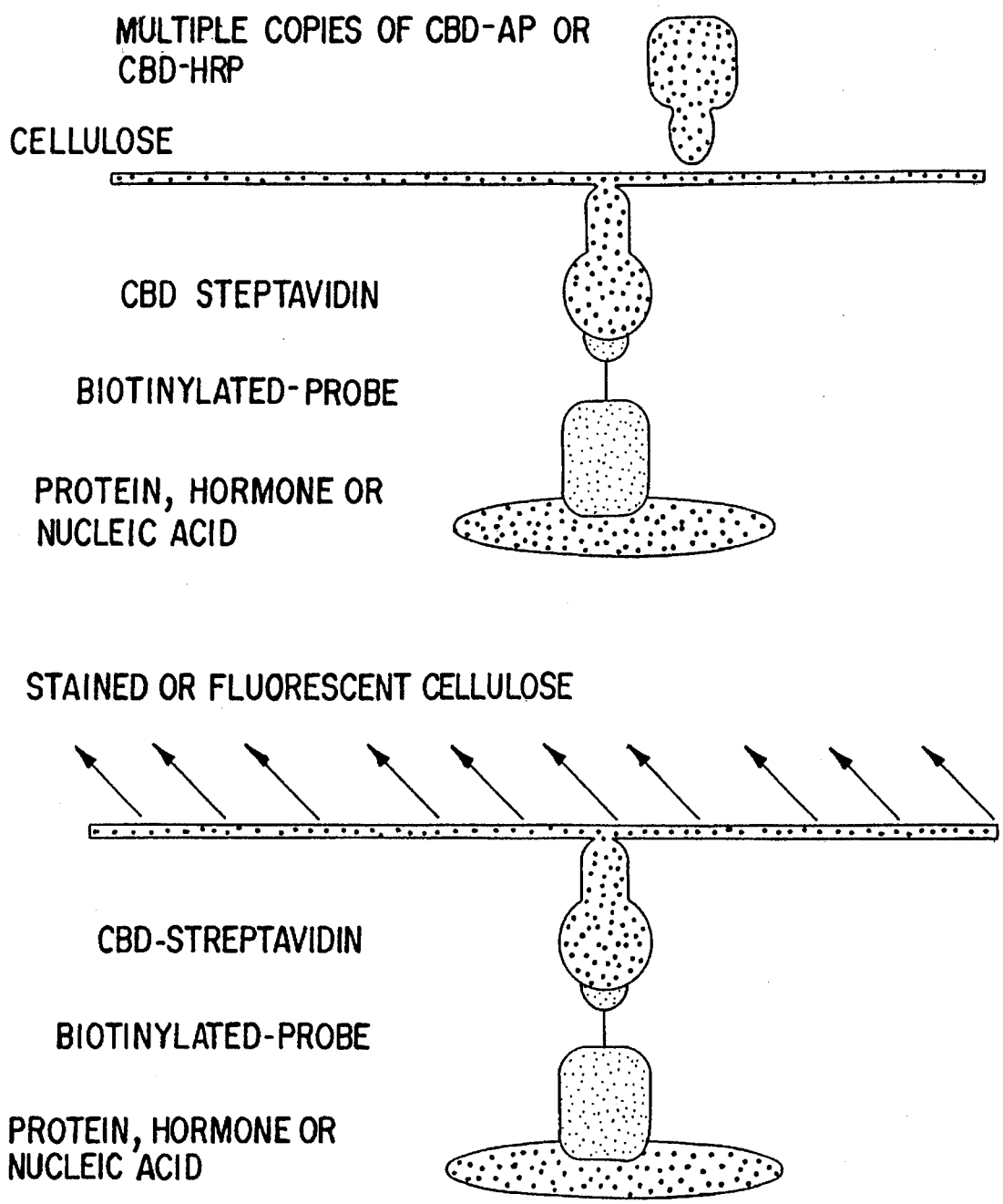

FIG. 11. Schematic of a signal amplification system in which labeled CBD detects cellulose or chitin to which is bound a CBD fusion product. The substance of interest is bound, in turn, to a chimeric probe.

Figure 12:
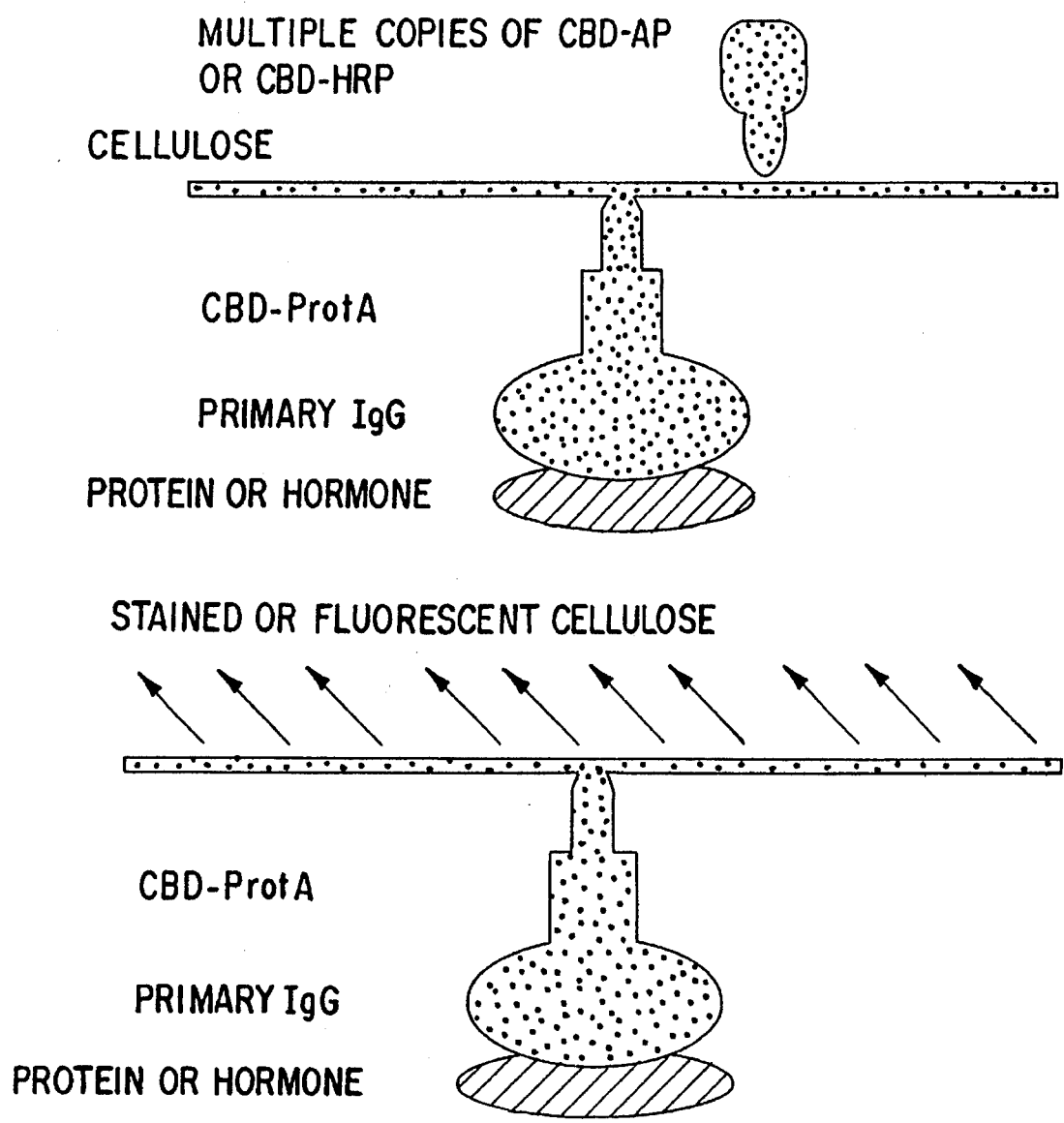

FIG. 12. Schematic of a signal amplification system in which the substance of interest is bound to a ternary CBD fusion product: CBD-ProteinA(IgG).

5. DETAILED DESCRIPTION OF THE INVENTION DEFINITIONS

The present invention is directed to the identification of cellulose binding domain (CBD) protein that is capable of binding cellulose with high affinity and in a reversible manner. The CBD of the present invention may be used, for example, in the bio-immobilization of biologically active molecules to cellulose. The CBD of the present invention may be fused to a second protein to form a CBD fusion protein. The presence of a CBD protein in a CBD fusion protein allows for easy and selective purification of the CBD fusion protein by incubation with cellulose. Examples of second proteins include: Protein A, protein G, streptavidin, avidin, Taq polymerase and other polymerases, alkaline phosphatase, RNase, DNase, various restriction enzymes, peroxidates, glucanases such as endo-1,4-beta glucanase, endo-1,3-beta-glucanase, chitinases, and others, beta and alfa glucosidases, beta and alfa glucoronidases, amylase, transferases such as glucosyl-transferases, phospho-transferases, chloramphenicol-acetyl-transferase, beta-lactamase and other antibiotic modifying and degrading enzymes, luciferase, esterases, lipases, proteases, bacteriocines, antibiotics, enzyme inhibitors, different growth factors, hormones, receptors, membranal proteins, nuclear proteins, transcriptional and translational factors and nucleic acid modifying enzymes. Specifically, the CBD protein may be fused to an antibody or an antigenic determinant to form a CBD fusion product that is useful in diagnostic kits and in immunoassays.

Thus, for example, bodily fluids can be tested for the presence of particular antibodies (e.g., heat shock protein (HSP) antibody) by making use of a CBD and an HSP epitope. Conversely, an HSP protein, a cross-reactive HSP-related protein, or antigenic portions thereof can be detected using a CBD-HSP antibody fusion protein.

The term "CBD" or "CBD protein" or "cellulose binding domain protein" refers to a protein comprising the amino acid sequence shown in FIG. 1 and includes functional homologs and functional derivatives thereof, provided that the functional homolog or functional derivative possesses the capability of binding to cellulose with high affinity and in a reversible manner. The CBD of the present invention is provided substantially free of other proteins with which it is naturally associated, for instance, the balance of the major CpbA protein, discussed above. In addition, one or more predetermined amino acid residues in the polypeptide may be substituted, inserted, or deleted, for example, to produce a CBD having improved biological properties, or to vary expression levels. Some of the desired CBD proteins falling within the scope of the present invention may optionally possess covalent or non-covalent modifications of the naturally occurring molecule, including, but not limited to, glycosylation modifications. Through the use of recombinant DNA technology, the CBD proteins of the present invention having residue deletions, substitutions and/or insertions may be prepared by altering the underlying nucleic acid. The modifications or mutations that may be made in the DNA encoding the CBD of the present invention must not alter the reading frame and preferably will not create complementary regions that could produce secondary mRNA structure (See, European Patent Publication No. EP 75,444)

The CBD protein of the present invention is one having at least 70% sequence similarity to the amino acid sequence shown in FIG. 1 [SEQ ID NO: 2], preferably, at least 80% sequence similarity, more preferably, at least 90% sequence similarity, and most preferably, at least 95% sequence similarity. The term "X% sequence similarity" is not intended to be limited to sequences having a X% sequence similarity over the entire length of the protein. The 70% sequence similarity is also intended to include X% sequence similarity occurring in identified functional areas within the CBD protein of FIG. 1. An example of a functional area would be a defined set of amino acids having the ability to bind cellulose with high affinity and in a reversible manner. Such protein homologs may also be referred to herein as "CBD functional homologs." In one embodiment of the present invention, such a functional area may have about 100 amino acids. In another embodiment of the present invention, such a functional area may have about 50 amino acids. The most desirable CBD protein of the present invention is one comprised of the amino acid sequence shown in FIG. 1.

The term "CBD functional derivative" as used herein refers to any "fragment" "variant" "analogue" or "chemical derivative" of the CBD protein amino acid sequence shown in FIG. 1 which retains the capability of binding to cellulose with high affinity and in a reversible manner and is preferably between about 2 and about 160 amino acids in length, more preferably between about 25 and about 125 amino acids in length and most preferably between about 50 and about 100 amino acids in length.

The term "fragment" is used to indicate a CBD protein which is derived from the CBD protein shown in FIG. 1, and has a naturally occurring sequence. Such a fragment may be produced by proteolytic cleavage of the full-length protein. Alternatively, the fragment is obtained recombinantly by appropriately modifying the DNA sequence encoding the CBD protein to delete one or more amino acids at one or more sites of the C-terminal, N-terminal, and within the naturally occurring sequence. Fragments of the CBD protein can be screened for the ability to bind cellulose with high affinity and in a reversible manner to determine the identity or utility of a functional derivative.

The term "variant" as used herein is defined as a molecule in which the amino acid sequence, glycosylation pattern, or other feature of a naturally occurring molecule has been modified covalently or noncovalently and is intended to include mutants. Some of the variants falling within this invention possess amino acid substitutions deletions, and/or insertions provided that the final construct possesses the desired ability of binding cellulose with high affinity and in a reversible manner. Amino acid substitutions in the CBD protein may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Also included within the definition of variant are those proteins having additional amino acids at one or more sites of the C-terminal, N-terminal, and within the naturally occurring CBD sequence as long as the variant retains the capability of binding cellulose with high affinity and in a reversible manner.

The term "chemical derivative" as used herein refers to a CBD protein produced by chemical modification of naturally occurring or variant CBD protein. Illustrative of an example of a chemical modification would be replacement of H by an alkyl, acyl, or amino group.

The phrase "binding cellulose with high affinity" as used herein refers to the ability of the CBD protein to bind to cellulose with a $K_d$ in μM ranging from about 1.5 to about 0.8, preferably from about 1.4 to about 0.8. More preferably, the high affinity binding refers to the ability of the instant CBD to bind to crystalline cellulose with a $K_d$ of about 1.1 or less, most preferably about 1.0 or less.

The phrase "binding cellulose in a reversible manner" as used herein refers to the ability of the CBD protein to be released from the cellulose-CBD protein binding complex by releasing agents or solutions, such as 6M urea, 6M guanidine-HCl and other denaturing reagents, including nonionic surfactants. Preferably, however, those denaturing reagents are used which allow the released CBD or fusion product to be reconstituted. For example, the CBD may be reconstituted from the treatment with 6M urea or 6M quanidine-Hcl by subjecting the denatured protein to renaturing conditions described in Sections 6.1.4, 7.1.1, 7.2.1, and 8.1.4, below.

The term "CBD fusion protein" as used herein refers to the joining together of at least two proteins, a CBD protein and a second protein. In some embodiments of the present invention, the second protein may be fused or joined to a third protein. In the present invention, examples of second proteins include enzymes, such as nucleic acid modification enzymes, proteases, hormones or hormone precursors, polypeptides, peptides, antibodies, antigens, antigenic epitopes and variants thereof. In some preferred embodiments of the present invention, the second protein is Protein A; in other preferred embodiments of the present invention, the second protein is an HSP protein. One preferred embodiment of the present invention is a fusion protein comprised of CBD protein, Protein A or anti-HSP recombinant IgG.

The CBD fusion protein of the present invention may comprise an enzymatic or chemical cleavage site upstream and preferably adjacent the N-terminus of the second protein and/or an enzymatic or chemical cleavage site downstream and preferably adjacent the C-terminus of the second protein thereby providing a means for recovering the second protein from the CBD fusion protein through use of a cleaving agent.

The term "CBD fusion protein-cellulose binding complex" as used herein refers to the complex formed when cellulose binds the CBD protein of a CBD fusion protein.

"Nucleic acid" refers to a nucleotide sequence comprising a series of nucleic acids in a 5' to 3' phosphate diester linkage that may be either an RNA or a DNA sequence. If the nucleic acid is DNA, the nucleotide sequence is either single or double stranded. CBD protein encoding nucleic acid is RNA or DNA that encodes a CBD protein capable of binding cellulose with high affinity, is complementary to nucleic acid sequence encoding such CBD protein, or hybridizes to nucleic acid sequence encoding such CBD protein and remains stably bound to it under stringent conditions.

The phrase "nucleic acid encoding the CBD protein of the present invention" includes nucleic acid of genomic, cDNA, synthetic, and semi-synthetic origin which, by virtue of its origin or manipulation, is not associated with any portion of the polynucleotide to which it is associated in nature, and may be linked to a polynucleotide other than that to which it is linked in nature, and includes single or double stranded polymers of ribonucleotides, deoxyribonucleotides, nucleotide analogs, or combinations thereof, as long as the CBD being encoded retains its ability to bind cellulose with high affinity. The phrase also includes various modifications known in the art, including but not limited to radioactive and chemical labels, methylation, caps, internucleotide modifications such those with charged linkages (e.g., phosphorothioates, phosphorodithioates, etc.) and uncharged linkages (e.g., methyl phosphonates, phosphotriesters, phosphoramidites, carbamites, etc.), as well as those containing pendant moieties, intercalators, chelators, etc. as long as the CBD encoded by the nucleic acid retains the ability to bind cellulose with high affinity and in a reversible manner.

CBD encoding nucleic acid may be used to construct recombinant expression vectors capable of expressing the CBD protein or the CBD fusion protein of the present invention. A nucleic acid construct is capable of expressing a protein if it contains nucleotide sequences containing transcriptional and translational regulatory information and such sequences are "operably linked" to nucleotide coding sequences. "Operably linked" refers to a linkage in which the regulatory DNA sequences and the DNA sequence to be expressed are connected in such a way as to permit transcription and ultimately translation.

In constructing the CBD fusion protein expression vector, the nucleic acid encoding the CBD protein will be linked or joined to the nucleic acid encoding the second protein such that the open reading frame of the CBD protein and the second protein is intact, allowing translation of the CBD fusion protein to occur. CBD nucleic acid may be obtained from a variety of cell sources that produce cellulose binding domains that bind with high affinity and in a reversible manner or that produce CBD encoding mRNA. The preferred source of CBD encoding nucleic acid is *Clostridium cellulovorans*. The CBD encoding nucleic acid may be obtained as described in Section 6.1.

The nucleic acid encoding the CBD protein of the present invention may be obtained from isolated and purified RNA from cell sources or by genomic cloning. Either cDNA or genomic libraries of clones may be prepared using techniques well known in the art and may be screened for particular CBD encoding nucleic acid with nucleotide probes that are substantially complementary to any portion of the gene. If detection of CBD protein encoding conserved nucleotide regions is desired, nucleotide probes should be based on CBD nucleotide sequences conserved from species to species. If detection of CBD protein encoding unique nucleotide regions is desired, nucleotide probes should be based on unique CBD nucleotide sequences. Alternatively, cDNA or genomic DNA may be used as templates for PCR cloning with suitable oligonucleotide primers. Full length clones, i.e., those containing the entire coding region of the desired CBD protein may be selected for constructing expression vectors, or overlapping cDNAs can be ligated together to form a complete coding sequence. Alternatively, CBD-encoding DNAs may be synthesized in whole or in part by chemical synthesis using techniques deemed to be standard in the art.

Many vectors are available, and selection of the appropriate vector will depend on 1) whether it is to be used for nucleic acid amplification or for nucleic acid expression, 2) the size of the nucleic acid to be inserted into the vector, and 3) the host cell to be transformed with the vector. Each vector contains various components depending on its function (amplification of nucleic acid or expression of nucleic acid) and the host cell for which it is compatible.

The term "host cell" refers to those cells capable of growth in culture and capable of expressing a CBD protein or CBD fusion protein. The host cells of the present invention encompass cells in in vitro culture and include procaryotic, eucaryotic, and insect cells. A host cell strain may be chosen which modulates the expression of the inserted sequences, or modifies and processes the gene product in the specific fashion desired. Expression from certain promoters can be elevated in the presence of certain inducers (e.g., zinc and cadmium ions for metallothionine promoters. Therefore expression of the CBD protein or CBD fusion protein may be controlled. The ability to control expression will be important if the CBD protein or CBD fusion protein is lethal to a host cell. Modifications (e.g., phosphorylation) and processing (e.g., cleavage) of protein products are important for the function of the protein. Different host cells have characteristic and specific mechanisms for the post-translational processing and modification of protein. Appropriate cell lines or host systems can be chosen to ensure the correct modification and processing of the CBD protein or CBD fusion protein expressed. Preferably, the host cell should secrete minimal amounts of proteolytic enzymes.

In the present invention, a host cell is provided comprised of nucleic acid encoding the CBD protein or CBD fusion protein of the present invention that is capable of binding to cellulose with high affinity. The preferred host cell for cloning and expression of the CBD proteins of the present invention is a prokaryotic cell. Procaryotes are particularly useful for rapid production of large amounts of nucleic acid, for production of single-stranded nucleic acid templates used for site-directed mutagenesis, for screening many mutants simultaneously, and for nucleic acid sequencing of the mutants generated. An example of a prokaryotic cell useful for cloning and expression of the CBD protein of the present invention is *E. coli* strain XL1-blue from Stratagene. Another example of a prokaryotic cell useful for cloning and expression of the CBD fusion protein is *Staphylococcus aureus*.

Various expression vector/host systems may be utilized equally well by those skilled in the art for the recombinant expression of CBD proteins and CBD fusion proteins. Such systems include but are not limited to microorganisms such as bacteria transformed with recombinant bacteriophage DNA, plasmid DNA or cosmid DNA expression vectors containing the desired CBD coding sequence; yeast transformed with recombinant yeast expression vectors containing the desired CBD coding sequence; insect cell systems infected with recombinant virus expression vectors (e.g., baculovirus) containing the desired CBD coding sequence; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the desired CBD coding sequence; or animal cell systems infected with recombinant virus expression vectors (e.g. adenovirus, vaccinia virus) including cell lines engineered to contain multiple copies of the CBD nucleic acid either stably amplified (e.g., CHO/dhfr, CHO/glutamine synthetase) or unstably amplified in double-minute chromosomes (e.g., murine cell lines).

Vector components generally include, but are not limited to, one or more of the following: a signal sequence, an origin of replication, one or more marker genes, an enhancer element, a promoter, and a transcription termination sequence. The expression elements of these vectors vary in their strength and specificities. Depending on the host/vector system utilized, any one of a number of suitable transcription and translation elements may be used. For example, when cloning in procaryotic cell systems, promoters isolated from the genome of procaryotic cells, (e.g., the bacterial tryptophane promoter) may be used. Promoters produced by recombinant DNA or synthetic techniques may also be used to provide for transcription of the inserted sequences.

A signal sequence may be a component of the vector, or it may be a part of the CBD nucleic acid that is inserted into the vector. The signal sequence may be the naturally occurring CBD sequence or a non-naturally occurring sequence. The signal sequence should be one that is recognized and processed by the host cell. An origin of replication refers to the unique site of initiation of replication of a host organism. It is desirable for cloning and expression vectors to comprise a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g. ampicillin; complement auxotrophic deficiencies; or supply critical nutrients not available from complex media. One example of a selection scheme utilizes a drug to arrest growth of a host cell. Those cells that are successfully transformed with a heterologous gene express a protein conferring drug resistance and thus survive the selection regimen.

Expression and cloning vectors usually contain a promoter that is recognized by the host organism and is operably linked to the nucleic acid encoding the polypeptide of interest. Promoters are untranslated sequences located upstream (5') to the start codon of a structural gene (generally within about 100 to 1000 bp) that control the transcription and translation of a particular nucleic acid sequence, such as that encoding a CBD protein or CBD fusion protein, to which they are operably linked. Such promoters typically fall into two classes, inducible and constitutive. Inducible promoters are promoters that initiate increased levels of transcription from nucleic acid under their control in response to some change in culture conditions, e.g., the presence or absence of a nutrient or a change in temperature. At this time, a large number of promoters recognized by a variety of potential host cells are well known. These promoters are operably linked to nucleic acid encoding the polypeptide of interest by removing the promoter from the source nucleic acid by restriction enzyme digestion and inserting the isolated promoter sequence into the vector. Both the naturally occurring promoter sequence and many heterologous promoters may be used to direct amplification and/or expression of the polypeptide of interest. However, heterologous promoters are preferred, as they generally permit greater transcription and higher yields of expressed polypeptide of interest as compared to the naturally occurring promoter. In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene* 2: 95 [1977]). The pBR322 plasmid contains genes for ampicillin and tetracycline resistance and thus provides easy means for identifying transformed cells. The pBR322 plasmid, or other microbial plasmid, must also contain or be modified to contain promoters and other control elements commonly used in recombinant DNA construction.

Promoters suitable for use with prokaryotic hosts illustratively include the β-lactamase and lactose promoter systems (Chang et al., "*Nature*", 275:615 [1978]; and Goeddel et al., "*Nature*" 281:544 [1979]), alkaline phosphatase, the tryptophan (trp) promoter system (Goeddel "Nucleic Acids Res."8:4057 [1980] and EPO Appln. Publ. No. 36,776) and hybrid promoters such as the tac promoter (H. de Boer et al., "*Proc. Natl. Acad. Sci.* USA" 80:21–25 [1983]). However, other functional bacterial promoters are suitable. Their nucleotide sequences are generally known, thereby enabling a skilled worker operably to ligate them to nucleic acid encoding CBD (Siebenlist et al., "*Cell*" 20:269 [1980]) using linkers or adapters to supply any required restriction sites. Promoters for use in bacterial systems also will contain a Shine-Dalgarno (S. D.) sequence operably linked to the nucleic acid encoding CBD.

Expression vectors used in prokaryotic host cells will also contain sequences necessary for the termination of transcription and for stabilizing the mRNA.

Construction of suitable vectors containing one or more of the above listed components and including the desired coding and control sequences employs standard ligation techniques. Isolated plasmids or nucleic acid fragments are cleaved, tailored, and religated in the form desired to generate the plasmids required.

Particularly useful in the practice of this invention are expression vectors that provide for the expression of prokaryotic cells of nucleic acid encoding the CBD protein. In general, expression involves the use of an expression vector that is able to replicate efficiently in a host cell, such that the host cell accumulates many copies of the expression vector and, in turn, synthesizes high levels of a desired polypeptide encoded by the expression vector.

Host cells are transfected and preferably transformed with the above-described expression or cloning vectors of this invention and cultured in conventional nutrient media modified as appropriate for inducing promoters, selecting transformants, or amplifying the genes encoding the desired sequences.

"Transformation" means introducing nucleic acid into an organism so that the nucleic acid is replicable, either as an extrachromosomal element or by chromosomal integration. Unless indicated otherwise, the method used herein for transformation of the host cells is the method of calcium treatment using calcium chloride as described by Cohen, F. N. et al., *Proc. Natl. Acad. Sci.* (USA),69:2110 (1972).

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., *Nucleic Acids Res.* 9: 309 (1981) or by the method of Maxam et al., *Methods in Enzymology* 65:499 (1980).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

Prokaryotic cells used to produce the polypeptide of this invention are cultured in suitable media as described generally in Sambrook, et al. (1989) Electrophoresis buffers in *Molecular Cloning* (Nolan, C. ed.), Cold Spring Harbor Laboratory Press, NY, pp. B.23–24; Sambrook et al. (1989) Bacterial Media in *Molecular Cloning* (Nolan, C. ed.), Cold Spring Harbor Laboratory Press, NY, pp. A.1–4.

The selection of host cells producing a CBD protein or CBD fusion protein of the present invention may be identified by at least four general approaches:

(a) DNA-DNA, DNA-RNA or RNA antisense RNA hybridization: the presence of CBD proteins of the present invention can be detected by nucleic acid hybridization using hybridization probes and/or primers for PCR reactions comprising nucleotides that are homologous to the CBD coding sequence;

(b) the presence or absence of "marker" gene functions: the selection of host cells having nucleic acid encoding CBD protein of the present invention can be identified and selected based upon the presence or absence or certain marker gene functions, e.g., resistance to antibiotics. For example, if the CBD coding sequence is inserted within a marker gene sequence of the cloning or expression vector, recombinants containing that coding sequence can be identified by the absence of the marker gene function. Alternatively, a marker gene can be placed in tandem with the CBD nucleic acid sequence under the control of the same or different promoter used to control the expression of the CBD coding sequence. Expression of the marker in response to induction or selection indicates expression of the CBD coding of the CBD coding sequence.

(c) assessing the level of transcription as measured by the expression of CBD protein or CBD fusion protein mRNA transcripts in the host cell: transcriptional activity of the CBD coding region can be assessed by hybridization assays. For example, polyadenylated RNA can be isolated and analyzed by Northern blot using a probe homologous to the CBD coding sequence or particular portions thereof. Alternatively, total nucleic acids of the host cell may be extracted and assayed for hybridization to such probes; and (d) detection of the CBD protein or CBD fusion protein as measured by immunoassay and, by the ability of the protein to bind cellulose with high affinity and in a reversible manner. The expression of CBD proteins can be assessed immunologically, for example by Western blots or by immunoassays such as RIAs. The expression of CBD protein can be assayed by the ability of the expressed protein to bind cellulose with high affinity and in a reversible manner.

The expressions "cell" and "cell culture" are used interchangeably and all such designations include progeny and ancestors. It is also understood that all progeny may not be precisely identical in DNA content, due to deliberate or inadvertent mutations. Mutant progeny that have the same function or biological activity as screened for in the cell are included.

The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5× SSC (0.75M NaCl, 0.075M Sodium pyrophosphate, 5× Denhardt's solution, sonicated salmon sperm DNA (50 g/ml), 0.1% SDS, and 10% dextran sulfate at 42° C. with washes at 42° C. in 0.2× SSC and 0.1% SDS.

The term "recovery" as used herein refers to the ability of the cellulose CBD protein complex to release the CBD protein from the cellulose-CBD protein binding complex under certain conditions, which conditions include the use of releasing agents, for example, denaturing reagents, such as 6M urea or 6M guanidine-HCl. Any releasing agent that has the ability of releasing the CBD protein from the cellulose-CBD protein binding complex can be used to recover the CBD protein. Preferably, the CBD is only temporarily denatured and not irreversibly degraded by treatment with the releasing agent. Thus, the CBD is recovered by reconstituting the eluted protein, as described in Section 7.1.1, 7.2.1, or 8.1.4.

The use of the phrase "cleaving agents" as used herein refers to a reagent used to cleave the CBD protein or CBD fusion protein specifically so as to release or excise certain components, such as the second protein of a CBD fusion protein, as desired. Suitable cleaving agents herein include enzymes, such as endoproteases, prohormone convertases, e.g., PC1, PC2, furin, Kex2, subtilisn, or its mutants; and chemical agents, such as organic and inorganic acids, hydroxylamine, N-bromosuccinimide, and cyanogen bromide. Hydrolysis of peptide bonds catalyzed by a variety of proteolytic enzymes is taught in The Enzymes, 3rd Edition, Boyer, Ed., Academic Press, Vol. III [1971]; *Meth. Enzymology.*, Vol. XIX, Perlman and Lorand, Ed., New York: Academic Press [1970]; *Meth. Enzymol.*, Vol. XLV, Lorand, Ed. New York: Academic Press [1976]; Drapeau, *J. Biol. Chem.*, 253: pg. 5899–5901 [1978] and Drapeau, *Meth. Enzymology.*, 47: 89–9[1977]. For an extensive listing of chemical agents, see Witcop in *Advances in Protein Chemistry.*, Anfinsen et al., ed., vol. 16 pg. 221–321, Academic Press, New York [1961], including Table III on p. 226. Other cleavage agents suitable herein are deemed to be understood by those skilled in the art keeping in mind the desired junction for cleavage and whether the reagent can act on reduced or oxidized forms of CBD fusion proteins. Conditions used for cleavage of the CBD fusion protein will depend on the cleavage agent employed, and the conditions will be readily apparent to one skilled in the art given the cleavage agent employed.

The CBD fusion protein of the present invention is designed and constructed to comprise the codon(s) necessary to achieve cleavage by the desired cleaving agent at desired positions, i.e. upstream, preferably adjacent the N-terminus of the second protein of the CBD fusion protein or downstream, and preferably adjacent the C-terminus of the second protein or both if the second protein of the fusion protein is an internal amino acid of the fusion protein.

The term "glycosylation" and grammatical derivatives as used herein refers to the post-translational modification process of adding a series of sugar residues to proteins to produce glycoproteins. Glycosylation can occur in the cytosol, the endoplasmic reticulum, or the Glogi apparatus of mammalian cells. Alternatively, glycosylation can be accomplished by synthetic methods, for example by providing an appropriate glycosyl donor. See, e.g., Kahne, et al. *J. Am. Chem. Soc.*, vol. 111: pg. 6881–2 [1989].

This invention also relates to diagnostic detection of proteins of interest in test samples, especially in biological samples, such as tissue extracts or biological fluids, such as serum or urine through use of the CBD fusion protein of the present invention. The biological samples are preferably of mammalian origin and most preferably of human origin. A preferred protein of interest to be detected in a mammalian biological sample is an HSP protein, an HSP antibody, cross-reactive HSP-related proteins, or antigenic portions thereof. The presence of the HSP antibody in a mammalian biological sample, for example, may be predictive or indicative of insulin-dependent diabetes mellitus (IDDM). In one embodiment of the present invention, the CBD Protein A fusion protein is comprised of a third protein, an IgG antibody, for example, IgG anti-HSP, which is used to detect the presence of an antigen, for example HSP, in biological samples using a variety of immunoassay formats well known in the art. Alternatively, the second protein of the CBD fusion protein is comprised of an antigenic determinant, an epitope, useful in the detection of antibodies that recognize the antigenic determinant. A preferred epitope is the HSP protein.

Protein A is a protein found in the cell wall of *Staphylococcus aureus* that binds to the Fc portion of Ig molecules and thus precipitates the antibodies. Protein A has utility in immunoassays, such as an RIA or ELISA, where it is used to isolate antibodies or antigen-antibody complexes.

In the present invention, Protein A is a preferred second protein of a CBD fusion protein. A CBD-Protein A fusion protein has utility in diagnostic immunoassays that detect the presence of or measure the quantity or concentration of an antibody or an anitbody-antigen complex.

A CBD-Protein A fusion protein of the present invention also has utility in a diagnostic kit comprised of cellulose and a CBD-fusion protein wherein the CBD fusion protein component retains its ability to bind both cellulose and IgG of a second component, for example, an antibody-antigen complex or an antibody. The CBD fusion protein of the present invention also has utility as a means for affinity purification of antibodies or antigenic determinants, i.e. epitopes. A preferred antigenic determinant of the present invention is the HSP protein, related protein or antigenic portion thereof. Preferred second proteins of a CBD fusion protein include HSP protein or anti-HSP IgG. In the present invention, CBD-HSP epitope fusion proteins find utility in immunoassays designed to measure quantities of HSP antibody found in the serum of human mammals.

The "antibody" as used herein is meant to include polyclonal antibodies, monoclonal antibodies (MAbs), humanized or chimeric antibodies, single chain antibodies, anti-idiotypic (anti-Id) antibodies, and epitope-binding fragments of any of the above. An epitope refers to an antigenic determinant of an antigenic molecule.

The term IgG refers to a class of antibodies. IgG is a tetramer containing two light chains and two heavy chains that represents 80% of all immunoglobulins.

The term "detectable label" as used herein refers to any label which provides directly or indirectly a detectable signal and includes, for example, enzymes, radiolabeled molecules, fluoresors, particles, chemiluminesors, enzyme substrates or co-factors, enzyme inhibitors, magnetic particles. Examples of enzymes useful as detectable labels in the present invention include alkaline phosphatase and horse radish peroxidase. A variety of methods are available for linking the detectable labels to proteins of interest and include for example the use of a bifunctional agent, such as 4,4'-difluoro-3,3'-dinitro-phenylsulfone, for attaching an enzyme, for example, horse radish peroxidase, to a protein of interest. The attached enzyme is then allowed to react with a substrate yielding a reaction product which is detectable.

Falling within the scope of the present invention is a signal amplification method wherein the use of a detectable label comprised of a CBD protein allows for detection of femtogram quantities of the substance of interest. In this method, a first CBD protein is part of a CBD fusion product that is incubated with a cellulose fiber under conditions suitable for formation of a cellulose-CBD fusion product binding complex. Excess labeled CBD, for example, CBD fused or bound to an enzyme, such as horse radish peroxidase or alkaline phosphatase, or a fluoresor or chemical stain, is incubated with the cellulose-CBD fusion product binding complex under conditions suitable to allow binding of the excess labeled CBD. The binding of excess labeled CBD to the cellulose-CBD fusion product binding complex in effect allows for detection of very low quantities of substances of interest. In the signal amplification method of the present invention, the preferred cellulose fiber is a pebble-milled cellulose fiber. The pebble-milled cellulose fiber can be stained with a variety of chemical dyes or mixed with calcofluor that bind the cellulose and produce an intense bright blue fluorescence upon uv illumination.

Also falling within the scope of the present invention is the use of the Streptavidin/biotin detection system. Biotin is capable of forming a tight and, essentially, irreversible complex with Streptavidin. In this aspect of the present invention, a CBD fusion product comprised of a CBD protein fused to Streptavidin is provided. A nucleotide or protein is biotinylated through techniques deemed to be routine to those skilled in the art in order to form a biotinylated chimeric probe capable of binding a substance of interest. The biotinylated probe is incubated with a substance of interest, the CBD-Streptavidin is incubated with the biotinylated probe and a detectable label is used to measure the biotinylated probe and consequently the substance of interest. The detectable label may be as described above in the signal amplification method, or any label, such as a fluoresor or chemical stain.

6. EXAMPLE: EXPERIMENTAL PROCEDURE FOR CLONING OF THE PUTATIVE CELLULOSE BINDING DOMAIN

6.1 Materials and Methods

6.1.1 Bacterial Strains and Plasmids

*E. coli* Xl 1 Blue strain was from StrateGene (La Jolla, Calif.), and was used for all cloning experiments. *E. coli*

BL21 (DE3) and pET-8c were as described (Studier et al., *J. Mol. Biol.* vol. 189, pp. 113–130 [1986]).

6.1.2 Materials

PC buffer, pH 7, contained 50 mM $KH_2PO_4$, 10 mM $Na_3 3C_6H_5O_7$ (sodium citrate), and 1 mM $NaN_3$. TEDG buffer (Chang et al., *J. Bacteriol.* vol. 172, pp. 3257–3263 [1990]) contained 10 mM Tris, pH 7, 0.1 mM EDTA, 0.1 mM dithiothreitol, and 5% v/v glycerol. Although Tris has a low buffer capacity at pH 7, the buffer was suitable because hydrogen ions were neither produced nor used. Restriction endonucleases were from BRL (Bethesda, Md.). All other chemicals used were of the highest purity commercially available. AVICEL (microcrystalline cellulose) PH101 (lot #1117) was from FMC Corp. (Philadelphia, Pa.). Absorbant cotton was from the Seamless Rubber Co. (New Haven, Conn.). Cellulin fiber was from Weyerhaeuser (Tacoma, Wash.). Granular chitin from crab shells is available from Sigma. All other binding substrates were purchased from Sigma Chemical Co., St. Louis, Mo. Each of the polysaccharides was washed twice with PC buffer before use. Masses of the polysaccharides refer to their dry weights as supplied from the manufacturer, except for nigeran, cellulin, and cotton. These three binding substrates had large particle sizes which interfered with the assay. Nigeran was recrystallized by dissolving the solid in hot water, filtering, and cooling on ice. The sizes of the cellulin and cotton fibers were reduced by processing with a Gifford-Wood mini-mill for five minutes.

6.1.3 Cloning of Putative Cellulose Binding Domains

DNA primers complementary to the regions of cbpA (Shoseyov et al., *PNAS USA* vol. 89, pp. 3483–3487 [1992]) flanking the putative CBD (CbpA residues 28–189) were synthesized by a Gene Assembler Plus (Pharmacia). The forward primer contained an NcoI restriction site (recognition sequence: CCATGG) with the ATG in-frame with the gene fragment, to act as a translational start codon when cloned into the pET-8c vector cloning site. The reverse primer contained a stop codon and a BamHI site. Polymerase Chain Reaction (PCR) was performed using 20 pmol each primer, 200 μM dNTPs, and 1 ng cbpA DNA [cloned into vector pGEMEX-1 (Promega) as in (Shoseyov et al., 1992, supra)] as a template, in a total volume of 100 μl. Taq polymerase was from Amersham, using buffer conditions recommended by the manufacturer. PCR was carried out for 40 cycles as described (Innis et al., *Optimization of PCRs* In: PCR Protocols Ed. Innis et al., Pub. Academic Press, San Diego, pp. 3–12 [1990]). The PCR product was purified by phenol/chloroform extraction followed by ethanol precipitation and a wash with 70% ethanol, then dried by vacuum and resuspended in 27 μl distilled water. The DNA was then cleaved by NcoI and BamHI, and run on a 2.5% low melting point agarose (Nuseieve GTG, FMC) gel in TBE buffer (Sambrook, et al. (1989) Electrophoresis buffers in *Molecular Cloning* (Nolan, C. ed.), Cold Spring Harbor Laboratory Press, NY, pp. B.23–24. DNA bands stained by ethidium bromide were visualized by long-wave ultraviolet light and cut from the gel. The vector, plasmid pET-8c, was prepared by cleaving 1 μg of pET-8c DNA with NcoI/BamHI and cutting the linearized DNA band from the gel. Vector and insert DNAs were ligated by using 100 ng of vector DNA and 300 ng of insert with a Takara Ligation kit. The ligated plasmids were used to transform competent *E. coli* XL1-Blue strain, which were then plated on LB plates (Sambrook et al. (1989) Bacterial Media in *Molecular Cloning* (Nolan, C. ed.), Cold Spring Harbor Laboratory Press, NY, pp. A.1–4.) containing 100 μg/ml Ampicillin and 12.5 μg/ml tetracycline. After overnight incubation at 37° C., colonies were selected and grown in liquid LB media with ampicillin and tetracycline. Plasmid DNA from each culture was rescued as described (Sambrook, et al. (1989) in *Molecular Cloning* (Nolan, C. ed.), Cold Spring Harbor Laboratory Press, NY) and cleaved with restriction enzymes to verify the insertion of the gene fragment. The insert sequence was confirmed by DNA sequencing using the same procedures as those reported in Shoseyov et al. (1992) *PNAS USA* 89:3483–3487.

6.1.4 Expression of CBD

The overexpression vector (pET-CBD) enables us to overproduce the 17 kDa CBD in *E. coli* strain BL21(DE3). CBD was accumulated to at least 70 mg/liter in inclusion bodies. However, additional quantity of about 20 mg/liter of water-soluble CBD could be recovered from the water-soluble sonic extract of the *E. coli*. The cleared extract was mixed with (SIGMACELL 20 (20 micron average particle size cellulose)) cellulose; then the CBD-cellulose complex was washed by 1M NaCl solution as well as distilled water to remove non-specific proteins, and then pure CBD was eluted by 6M guanidine-HCl. CBD was fully renatured by slow dialysis at room temperature and regained its ability to bind to cellulose (FIG. 10. lane 2).

7. EXAMPLE: PURIFICATION OF CBD PROTEIN

7.1 Preparation of CBD Protein

7.1.1 Purification of CBD Protein

Plasmid DNA containing the insert was used to transform *E. coli* BL21 (DE3). Plasmid-containing cultures were grown at 37° C. in NZCYM (Sambrook, et al. (1989) in *Molecular Cloning* (Nolan, C. ed.), Cold Spring Harbor Laboratory Press, NY) medium containing ampicillin (100 μg/ml) with shaking to Klett reading 160 (green filter). At this point, IPTG was added to a final concentration 1 mM. After 4 h, the cells were harvested by centrifugation, resuspended in 50 mM phosphate/12 mM citrate pH 7 (PC) buffer containing RNAse A at 10 μg/ml and DNAse I at 1 μg/ml, and lysed by sonication on ice with a Biosonic II sonicator at maximum power for 45 s followed by a 15 s cooling period, repeated a total of 4 times. The insoluble fraction of a 1 l cell culture was collected by centrifugation (30 min at 12,000 g, 4° C.) and resuspended in 20 ml of 6M guanidine HCl. This was kept on ice for 30 min with occasional vortexing to disperse the pellet. Insoluble debris was removed by centrifugation (30 min at 12,000 g, 4° C.). The soluble guanidine HCl extract was gradually diluted to 400 ml total volume with TEDG renaturation buffer over a two h period at 4° C. Ammonium sulfate was added to 80% saturation After four h at 4° C. precipitated proteins were collected by centrifugation (30 min at 12,000 g, 4° C.), resuspended in 40 ml PC buffer, and dialyzed against PC buffer.

Further purification of the CBD protein fragment of CbpA was carried out by affinity chromatography on cellulose: Three additions of 1.0 g AVICEL® PH101 microcrystalline cellulose were used to remove the CBD protein from the solution. After each addition, the suspension was allowed to come to equilibrium (1 h at room temperature with slow rotation). The cellulose was then collected by centrifugation and removed before the next addition. The three grams of cellulose were washed once by 1M NaCl/PC buffer and twice by PC buffer. Purified CBD was eluted from the cellulose by three washes with 10 ml 6M urea. The urea fractions were pooled and dialyzed against PC buffer (4° C. to about ambient temperature). Protein concentration in the final purified fraction was analyzed by colorimetric methods using the MicroBCA protein assay kit (Pierce, Rockford, Ill.), using bovine serum albumin (BSA) standards.

7.1.2 Determination of the CBD-Cellulose Dissociation Constant and the Cellulose Binding Capacity Samples of CBD protein (typically 0 to 100 μg) were added to 1.5 ml capacity microfuge tubes containing PC buffer supplemented with 1 mg/ml BSA and the desired amount of cellulose (typically 1 mg added from a stock slurry containing 10 mg/ml cellulose and 1 mg/ml BSA in PC buffer). Potential competitors, e.g. cellobiose (4 mg/ml) or carboxymethylcellulose (CMC, 4 mg/ml) were included by adding 200 μl of a 20 mg/ml stock solution in PC/BSA buffer. The final volume was always 1 ml. The pH of the buffer was 7.0 unless otherwise noted. For experiments at other pH values, the PC/BSA buffer was adjusted by the addition of concentrated HCl or NaOH.

Assay tubes were mixed by slow vertical rotation (30 RPM) at 37° C. for one h. The samples were then spun in a microfuge for one min to sediment the cellulose and cellulose-protein complexes. After removing the buffer, the pellet was washed by resuspension in 1 ml of PC buffer. The wash was separated out by centrifugation and discarded. Pellets were then resuspended in a final 1 ml PC buffer. (The centrifugation step would not be expected to perturb the equilibrium because the [C] and [PC] were concentrated to the same extent.)

Of the original BSA in the assay tubes (ca. 1 mg/ml), only about 0.1 μg would remain after the washing steps assuming no non-specific adsorption and a liquid volume of 10 μl in the pellet. Any color development due to this residual BSA was accounted for by the 0 CBD control tubes. Aliquots (150 μl) of this well-mixed suspension were taken for protein determinations with the MicroBCA kit. The manufacturer's instructions were followed, except that the sample volume was brought to 0.5 ml with PC buffer, to which 0.5 ml of BCA working reagent was added. Assay mixtures were incubated at 60° C. for 30 min. The protein concentration was determined colorimetrically from the cleared supernatants at 562 nm in a Shimadzu 160 U spectrophotometer. Assay tubes to which no CBD protein was added were used to correct for a small amount of color development caused by the cellulose and residual BSA. The data were compared to BSA standards and adjusted to accommodate the dilutions that were made to determine the amount of protein bound to the cellulose in each sample. The practical detection limit of this assay was about 0.2 μg/ml. After correction for dilutions, this corresponds to about 0.034 nmol of CBD bound to the cellulose in the assay tube. The free CBD protein concentration, [P], was determined by subtracting the bound protein concentration, [PC], from the total CBD added to the tube, $[P]_t$:

$$[P] = [P]_t - [PC] \tag{1}$$

The system was analyzed assuming a simple equilibrium interaction (Segel, 1975):

$$P + C \underset{k_{-1}}{\overset{k_1}{\rightleftharpoons}} PC \tag{2}$$

where the dissociation constant, $K_d$, is defined as:

$$K_d = \frac{k_{-1}}{k_1} = \frac{[P][C]}{[PC]} \tag{3}$$

The data were analyzed by double reciprocal plots of 1/[PC] versus 1/[P] at different fixed levels of cellulose (equation 4) and W:

$$\frac{1}{[PC]} = \frac{1}{K_d} \cdot \frac{1}{[P]} + \frac{1}{[PC]_{max}} \tag{4}$$

and by Scatchard plots of [PC]/[P] versus [PC]:

$$\frac{[PC]}{[P]} = \frac{-1}{K_d}[PC] + \frac{[PC]_{max}}{K_d} \tag{5}$$

It must be noted that the cellulose is not a soluble component, and that [C] represents the concentration of binding sites on the cellulose surface exposed to the buffer, per unit volume. Similarly, the [PC] represents the concentration of binding site-protein complexes per unit volume. Straight lines were fitted to the data points by the least-squares method using DeltaGraphProfessional plotting application (Deltapoint, Inc., Monterey, Calif.). Each point was the average of three independent protein assays from the same binding assay tube. Experiments were performed in duplicate. At least two different amounts of cellulose were used to determine the $K_d$ and $PC_{max}$/g cellulose. These values were averaged to provide the listed values in Table I, FIG. 9.

7.1.3 Determination of Binding to Other Polysaccharides

Xylan, nigeran, SEPHADEX (cross-linked Dextran) G-75, and chitin were used in assays to determine whether they were substrates for CBD protein. In all cases, the methods used were the same as those used in determining the binding to cellulose. Chitin exhibited a very high background in the MicroBCA assay, which increased proportionally to the 60° C. incubation time, so the color development time was reduced to 15 min. Because of chitin's high background, only two widely different protein concentrations were used.

7.2 Results

7.2.1 Purification of the CBD for Binding Analyses

In order to selectively produce the putative CBD region of CbpA (residues 28–189), oligonucleotide primers were designed complementary to bases 67 to 86 and 558 to 579 of cbpA (FIG. 1). As shown in FIG. 2, these primers were designed with mismatches to create an NcoI site and an ATG start codon on one end of the PCR product and a TAG stop codon followed by a BamHI site at the other end. This gene fragment was then cloned into the T7 RNA polymerase expression plasmid pET-8c, resulting in plasmid pET-CBD. See, Studier, F., and B. A. Moffatt (1986) *J. Mol. Biol.* 189: 113–130. The cloned gene fragment codes for a methionine at the N-terminus of the CBD, but the rest of the CBD aa sequence corresponds to residues 28 to 189 of CbpA. The protein fragment has a molecular weight of 17634. The insertion was verified by DNA sequencing. CBD protein was produced by *E. coli* BL21 (DE3) cells harboring pET-CBD. After the addition of IPTG, this host strain produces T7 RNA polymerase, which recognizes the T7 promotor in the pET vector. The cbd gene fragment was under the control of this inducible promotor, and CBD protein was synthesized in large amounts after induction (FIG. 3). After a four h production period, the soluble extract from the lysed cells contained only small amounts of CBD protein, while most was found in the insoluble fraction. This protein was readily soluble in concentrated guanidine hydrochloride, and was renatured by slow dilution into TEDG buffer. It was found that protein prepared in this fashion binds to AVICEL (microcrystalline cellulose), verifying the putative CBD. Although this fraction is mostly CBD protein, the assays described require the protein to be highly pure. This purity is provided by a single cellulose-affinity binding step, as described in the Section 7.1.1. The affinity-purified CBD protein appears on acrylamide gels as a single band when stained with Coomasie brilliant blue. Approximately 70 mg of CBD protein can be recovered from the cells harvested from a 1 l culture.

7.2.2 Time course of the Binding of the CBD to Cellulose

The time course of the interaction of AVICEL (microcrystalline cellulose) with CBD (FIG. 4) discloses several features of the process:

(a) At initial concentrations of 1.0 mg/ml Avicel® and 2.0 µM CBD (i.e., $[P]_o$), a plateau value of 1.2 µM complex (i.e., [PC]) is attained by 60 minutes. A separate experiment established that the maximum CBD binding capacity of the cellulose sample was 2.1 µmoles×g$^{-1}$, corresponding to an effective concentration of 2.1 µM total cellulose sites (i.e., $[C]_o$). Assuming that an equilibrium was established (verified below), $K_d$ defined as [P] [C]/[PC] is about 0.6 µM.

(b) The second-order rate constant for association ($k_1$) calculated from the integrated rate equation for a reversible Bi Uni reaction (Capellos & Bielski, 1980; Wilkinson, 1980) is about 2.7×10$^4$ M$^{-1}$×min$^{-1}$ (average value for points from 5–60 min). The rate constant for the dissociation of the complex ($k_{-1}$) calculated as k$^1$K$_d$ was 1.6×10$^{-2}$×min$^{-1}$ ($t_{1/2}$=43 min). The relatively long $t_{1/2}$ for complex dissociation permitted the C+PC pellet to be washed once without significant loss of bound CBD. (Resuspension and recentrifugation of the initial pellet was completed in less than 1 min. During this period, less than 3% of the bound CBD would be lost.) It was also observed that after prolonged incubation, the measured [PC] declined, dropping to a level of about 50% of the maximum value after 18 hours. This decline may be caused by gradual denaturation of the protein. To reduce artifacts resulting from these effects, we used the shortest incubation time for which equilibration appeared to be "complete". (Any further increase in binding beyond 60 min would be obscured by the experimental error.)

7.2.3 Analysis of the CBD-Cellulose Binding Affinity and Binding Capacity

FIG. 5 shows a typical diagnostic plot of the binding of pure CBD to AVICEL microcrystalline cellulose. Within experimental error, the plots were linear yielding a $K_d$ of about 0.6 µM and a $[PC]_{max}$ of 2.1 µmoles CBD bound per gram AVICEL (microcrystalline cellulose). The latter value corresponds to approximately 37 mg of CBD protein per gram of AVICEL (microcrystalline cellulose). The linearity of the diagnostic plots suggests that only one type of CBD-cellulose interaction is occurring.

The ability of CBD to bind cellulose types other than AVICEL (microcrystalline cellulose) was also investigated. Table 1, FIG. 9, shows the values for the $K_d$ and $PC_{max}$ found for each of the substrates. SIGMACELL 20 and 50 are described as microcrystalline forms of cellulose; these materials were also found to bind to CBD. Highly crystalline forms of cellulose such as absorbant cotton and CELLULON® fiber (crystalline cellulose from Acetobacter xylinum) were able to bind substantially more of the CBD (up to 6.4 µmol CBD per gram of substrate). Fibrous and microgranular cellulose, however, which are more processed and thus contain less of the native crystalline form, were found to bind a smaller amount of the CBD. The CBD-cellulose dissociation constant was about the same for all forms of cellulose, while the $PC_{max}$ varied over a 30-fold range.

7.2.4 Binding Site Competition

To determine if soluble carbohydrates competed with AVICEL (microcrystalline cellulose) for the CBD protein, cellobiose (a β-1,4 linked glucose dimer) and CMC (a soluble derivative of cellulose) were included in some assays at 4 times the weight/volume of AVICEL (microcrystalline cellulose) (1 mg Avicel®, 4 mg cellobiose or CMC per ml assay). As Table 1, FIG. 9, shows, no significant differences in the $K_d$ or $PC_{max}$ were observed, indicating these soluble carbohydrates did not affect the binding of the CBD to AVICEL (microcrystalline cellulose).

7.2.5 Effect of pH on the Dissociation Constant

*C. cellulovorans* is a neutrophilic organism, thriving only around pH 7 (Sleat et al., 1984), so this pH was used for most of the binding assays. However, other experiments established that the $K_d$ and $PC_{max}$ did not vary significantly with changes in pH over the range 5.0 to 8.0. In addition, it was noted that PC buffers as acidic as pH 3.5 or as basic as 9.5 would not remove the CBD from AVICEL (microcrystalline cellulose) during 1-min washes.

7.2.6 Binding of the CBD to Other Polysaccharides

Xylan, SEPHADEX (cross-linked Dextran) G-75, nigeran, and chitin were used to explore the binding specificity of the CBD. Of these, only chitin showed measurable binding of the CBD peptide Table 1, FIG. 9. The chitin-CBD $K_d$ and binding capacity were similar to the AVICEL (microcrystalline cellulose)-CBD values.

7.3 Results

Our results show that CbpA contains a domain responsible for cellulose binding, and that this domain could function independently from the rest of CbpA. Because the purification protocol employed denaturation and renaturation steps, the fact that the purified protein was functional indicates that the CBD protein sequence was sufficient for proper folding of the protein fragment.

We have found non-specific binding of the CBD to the assay tubes to be a problem in performing equilibrium binding experiments, and have developed an assay in which the CBD and cellulose are equilibrated in the presence of excess BSA. The BSA effectively eliminates non-specific CBD interactions with the tube. After equilibrium is reached, the cellulose and cellulose-protein complexes are collected and washed, then assayed for bound proteins. As described earlier, the dissociation of the CBD-cellulose is slow so that no detectable amount is removed during a rapid wash step.

The bound CBD was measured directly by the protein assay, and the free CBD was calculated by subtracting the bound CBD from the total CBD, as shown in equation 1, Section 7.1.2. This method has the advantage that any CBD molecules adsorbed non-specifically with low affinity to the cellulose would be removed by the wash step, resulting in data that more accurately reflect the specific, high affinity interaction between the CBD and the cellulose surface. As shown in FIG. 5, data gathered using this type of assay yields (within experimental error) linear diagnostic plots. Double reciprocal plots are a convenient and conventional way of determining binding affinities and capacities for reversible Bi uni systems. The validity of the assay is supported by the observation that $PC_{max}$ increases linearly with the amount of cellulose used, while $K_d$ is independent of the cellulose quantity. Table 1, FIG. 9, shows the results obtained with several forms of cellulose and other carbohydrates. The results indicate that cellulose types described as "crystalline" have a higher CBD binding capacity than highly processed celluloses that have lost much of their crystallinity. The fact that the $PC_{max}$ of cellulose samples vary widely with different cellulose types while the $K_d$ remains constant indicates that we have measured one type of strong protein-cellulose interaction occurring between the CBD and the cellulose. The lower $PC_{max}$ of highly processed celluloses reflects a smaller number of potential protein interaction sites in the sample, and seems to correlate with the crystallinity of the sample. This result would indicate, although not wishing to be limited by theory, that there is some special feature present in crystalline cellulose that makes it acceptable as a binding substrate, whereas amorphous cellulose is found lacking.

To further characterize the substrate specificity of the CBD, we measured the effect of added soluble substrates (cellobiose or CMC) on cellulose binding. Excess cellobiose or CMC had no effect on the CBD-AVICEL (microcrystalline cellulose) $K_d$ or $PC_{max}$, as shown in Table 1, FIG. 9. This lack of competition suggests that the CBD recognition site is specific for something more complex than a simple repeating glucose or cellobiose moiety, and further suggests that, perhaps, a particular three-dimensional arrangement of cellulose chains is needed.

The specificity of the CBD for crystalline cellulose prompts a consideration of chitinases, which are known to bind tightly to chitin, a polymer of N-acetylglucosamine in β-1,4 linkage. Like cellulose, chitin comes in a variety of forms, depending on the source and purification method used in its isolation (Cabib (1988) *Methods Enzymol.* 161:460–462; Blackwell (1988) *Methods Enzymol.* 161:435–442). The chitin used for affinity purification of chitinases is α-chitin, in which the chains are arranged in an antiparallel fashion. This form of chitin is crystalline with a structure similar to that of native crystalline cellulose (often referred to as cellulose I). Cellulose I is the form in which the cellulose chains are arranged in parallel bundles, as opposed to cellulose II, in which the chains are in an antiparallel configuration. Processing of cellulose I under harsh conditions causes its disruption resulting in cellulose II. Both forms are crystalline, due to extensive hydrogen bond formation. Since our isolated CBD binds to less processed forms of cellulose, i.e., largely cellulose I, we were interested to see if the CBD would bind to α-chitin, which has a similar crystal structure, although of opposite strand orientation. Surprisingly, we found that the CBD did accept chitin as a binding substrate with a $K_d$ very similar to that for cellulose. Xylan (β-1,4 xylose), nigeran (alternating a-1,4 and a-1,3 glucose), and SEPHADEX (cross-linked Dextran) G-75 (a-1,6 glucose with a-1,3 branches) (Coutinho et al. (1992) *Mol. Microbiol.* 6:1243–1252) were also examined, but the CBD did not show measurable binding to any of them under the conditions of the assay. Since chitin is the only one of these substrates that is crystalline, we feel that this demonstrates the importance of crystallinity in the substrate.

Although this is certainly a part of the benefit of tight substrate binding, recent studies (Din et al. (1991) *Bio/Technol.* 9:1096–1099) have shown that binding to cellulose by isolated, non-enzymatic CBDs causes disruption of the cellulose fibers in a non-hydrolytic fashion. It is thought that the protein-cellulose binding lowers the degree of interchain hydrogen bonding near the surface of the crystal, which is followed by extensive hydration of these cellulose chains. The end result is a decrease in crystallinity. This process, termed "amorphogenesis," renders more of the cellulose fiber accessible to the endo-β-1,4-glucanases. As we have discovered, the CBD exhibits no such amorphogenic effect.

8. CONSTRUCTION OF CBD-ProtA GENE AND ITS EXPRESSION IN *E. COLI*

8.1 Material and Methods

8.1.1 Enzymes and Chemicals

Chemicals were purchased from Sigma Chemicals Inc. unless stated otherwise. Restriction enzymes were purchased from New England Biolabs, Inc. Taq polymerase was purchased from Promega, Inc.

8.1.2 Plasmids and Bacteria

The plasmid pCB1 carrying cbpA (Shoseyov et al. 1992) was used to amplify cbd by PCR methods. The expression vector pRIT2 (Nilsson, et al (1985) *EMBO J.* 4(4):1075–1080) was used for the construction of the fusion genes. Initial transformations were conducted using *E. coli* strain XL1-blue (Strategene). Expression of CBD-ProtA was conducted in the temperature sensitive repressor containing strain, 2097. Also, *E. coli* strain N4830-1 carries the temperature-sensitive repressor ci857 and is equivalent to *E. coli* strain 2097. The *E. coli* strain N4830-1 is available from Pharmacia, Inc.

8.1.3 Cloning of CBD-ProtA

CBD was PCR amplified using cbpA gene as a template. Primers A (N-terminal primer [SEQ ID NO: 14]; '5-GGGG-GAATTCCATGGCAGCGACAT-'3) contain EcoRI site, primer B (C-terminal primer [SEQ ID NO: 15]; '5-GGGGG-GATCCTATGGTGCT-'3) contain a stop codon followed by a BamHI site. The primers were designed and synthesized in a way that enable force cloning of EcoRI/BamHI 500 bp DNA fragment into the plasmid pRIT2 "in frame" fused to the C-terminal part of Protein A gene. PCR conditions were as described by Innis and Gelfand (1990) with the following modifications: 2 ng template DNA (cbpA) and 1 mM $MgCl_2$ were used in the reaction mixture. The reaction was conducted using a programmable thermal controller (M&J Research Inc.). Standard DNA manipulations were conducted according to Sambrook et al (1989) in Molecular Cloning (Nolan, C. ed.), Cold Spring Harbor Laboratory Press, NY. The PCR amplified product was digested with EcoRI and BamHI, and the expected 500 bp DNA fragment (FIG. 1) was isolated from 1.5% agarose gel using QIAEX gel extraction kit (Qiagen Inc.). The EcoRI/BamHI fragment was ligated into EcoRI/BamHI linearized pRIT2 using T4 Ligase. The ligation mixture was used to transform XL1-Blue competent cells and transformed colonies were selected on LB agar plates containing 100 mg/l ampicillin. Successful construct containing the DNA insert was designated pCBD-ProtA1.

8.1.4 Expression and purification of CBD-ProtA

Expression of the fusion protein was conducted as described elsewhere (Nilsson, et al (1985) *EMBO J.* 4(4):1075–1080). 40 ml LB containing 50 mg/l ampicillin was inoculated with 400 ul of overnight culture of *E. coli* strain 2097 containing pCBD-ProtA1. The culture was grown to 100 Klett (green filter) at 30° C. and then shifted to 42° C. for 45 minutes and then grown for additional 2 hours at 40° C. The cells were harvested by centrifugation at 2,000 g for 10 min. and resuspended in 10 ml of 20 mM Tris-HCl buffer pH 7. The cells were lysed using W-385 sonicator (Heat Systems-Ultrasonic, Inc.) at maximum power for 1 minute followed by a 30-second cooling period, repeated 3 times. The lysate was cleared by centrifugation (4,000 g for 10 min) and 500 mg of cellulose particles (Sigmacell 20, 20 microns average particle size) were added. The suspension was incubated for ten minutes at RT and centrifuged (2,000 g for 10 minutes). The supernatant was removed and the pellet was washed once with 5 ml of 1M NaCl to remove non-specific binding proteins and twice with 10 ml of deionized water. CBD-ProtA was remove from the cellulose by 5 ml 6M guanidine-HCl. After centrifugation (2,000 g, 10 min) the solution was then dialysed against 20 mM Tris-HCl buffer (pH 7). Proteins were analyzed on 12.5% SDS-PAGE according to Laemmli (1970).

8.1.5 Binding Analysis of CBD-ProtA

The binding of CBD-ProtA to IgG was determined as follows: A 100 μl suspension of rabbit IgG (H+L)-Sepharose (8 mg/ml, Bio-Makor Inc.) that was prewashed with PBS (Phosphate Buffer Saline pH 7.4) was mixed with 1 ml of isolated CBD-ProtA (50 μg/ml). The mixture was incubated for 1 hour at 8° C. and then centrifuged (2,000 g, 5 minutes). The supernatant was removed and the pellet was washed twice with 500 μl of PBS. Then, the CBD-ProtA was eluted with 200 μl of 1M acetic acid. The pellet was mixed with 15 μl of sample application buffer (SAB; 125 mM Tris-HCl pH 6.8, 4% SDS, 20% glycerol and 0.002% bromophenol blue), 15 μl samples of the different fractions were mixed with 15 μl of SAB, then boiled for 5 minutes and analyzed on SDS-PAGE.

The binding of CBD-ProtA to cellulose was determined as follows: 20 mg of cellulose SIGMACELL 20 (20 micron average particle size cellulose) were mixed with 200 μl of isolated CBD-ProtA (50 μg/ml). The mixture was incubated for 15 min at RT and centrifuged at 2,000 g for 5 min. The pellet was washed with 200 μl 1M acetic acid and the pellet was resuspended with 40 μl of SAB. The cellulose suspension was boiled along with the 15 μl of the acetic acid wash (mixed with 15 μl SAB) and analyzed on SDS-PAGE.

8.1.6 Results

It was shown that CBD-ProtA can be expressed in *E. coli* and purified using cellulose in a one-step purification. The fusion protein has the expected size, 45 kDa (FIG. 8).

CBD-protA retained its affinity to cellulose as well as to IgG. It was shown that 1M acetic acid releases the CBD-ProtA:IgG bond but not the CBD-ProtA:cellulose bond.

Using this expression vector, we produced 6 mg of CBD-ProtA per 1 liter of culture. Our experience with the T7 overexpression system enabled us to produce more then 10 times that amount (70 mg/l) of pure CBD (FIG. 10).

9. CLONING OF CBD-HSP FUSION PROTEIN

An example for the cloning of CBD-HSP fusion protein: PCR primers for the amplification of HSP gene are prepared using the plasmide SJ60 as a template. The vector was described by Jindal et al. (1989) *Mol. Cell. Biol.* 9:2279. The primers will contain KpnI site at the N terminal of HSP and stop codon followed by a BamHI site at the C terminal.

Forward primer [SEQ ID NO: 16]: 5'-ACGGTACCACT-TCGGTTACCCACAGTC-3'

Reverse primer [SEQ ID NO: 17]: 5'-GGGGATCCTA-CATGCCACCTCCCATTAG-3'

In order to enable translational fusion of the C terminal part of CBD to the N terminal part of HSP, we introduce a KpnI site at the 3' end of cbd gene. This introduction achieves PCR amplification of cbd using pET-CBD as a template and the following primers:

Forward primer [SEQ ID NO: 4]: 5'-GTATACCAGC-CATGGCAGCG-3'

Reverse primer [SEQ ID NO: 18]: 5'-GTACATCTG-GATCCTATGGTACCGT-3'

The amplified DNA is digested with NcoI and BamHI and is then ligated into NcoI/BamHI predigested pET8c vector. The ligation mixture is then used to transform XL1Blue and the new plasmid designated as pET-CBDK. This plasmid is digested with KpnI and BamHI and the KpnI/BamHI restricted HSP-PCR amplified fragment is ligated; transformed into XL1Blue and after conformation of the construct will be used to transform BL21(DE3) for overproduction of CBD-HSP.

10. CONSTRUCTION OF $NH_2$-$V_H$-$V_L$-CBD-$CO_2$

CBD fused to recombinant antibody is carried out by cloning any desired $V_H$-$V_L$ using the "Recombinant Phase Antibody System" (Pharmacia Inc.). The resulting pCANTAB5 plasmid carrying the $V_H$-$V_L$ is used as a template for PCR amplification using the following primers:

Forward primer [SEQ ID NO: 19]: 5'-AGCCATGGCG-GCCCAGC-3'

Reverse primer [SEQ ID NO: 20]: 5'-GGGGTACCAA-CAGTTTGTGCGGCC-3'

These primers introduce the NcoI site at the 5' of the $V_H$-$V_L$ and KpnI site at the 3' end. The amplified fragment is digested (partially if necessary) with NcoI and KpnI and is used in the expression vector of C-terminal fusion of CBD, below.

To enable translational fusion of the N terminal part of CBD to the C terminal part of $V_H$-$V_L$, we introduce a KpnI site at the 3' end of cbd gene. This introduction is achieved by PCR amplification of cbd using pET-CBD as a template and the following primers:

Forward primer [SEQ ID NO: 21]: 5'-GGGCCATG-GCAGGTACCTCATCA-3'

Reverse primer [SEQ ID NO: 9]: 5'-GTACATCTG-GATCCTATGGTGCTGT-3'

These primers introduce KpnI sit at the 5' end of cbd gene after the NcoI site, and maintain the stop codon followed by BamHI site at the 3' end. The amplified DNA is digested with NcoI and BamHI and then is ligated into NcoI/BamHI predigested pETSc vector. The ligation mixture is used to transform XL1Blue and the new plasmid is designated as pET-KCBD. This plasmid is digested with NcoI and KpnI and the NcoI/KpnI restricted $V_H$-$V_L$ amplified fragment is then ligated; transformed into SL1Blue and after conformation of the construct is used to transform BL21(DE3) for overproduction of $V_H$-$V_L$-CBD fusion protein.

In view of the above-disclosure and what is generally known in the art, it would be apparent to one of ordinary skill that a wide variety of CBD fusion products can be prepared which comprise the CBD and second proteins of known sequence.

Furthermore, these clearly demonstrate the usefulness of CBD fusion proteins for affinity purifications of proteins and enzymes using cellulose as the insoluble solid matrix. Furthermore, it is also contemplated that the CBD fusion products offer a wide range of potential applications that would be apparent to one of ordinary skill in view of the above disclosure, including affinity separation methods and use in diagnostic kits.

The following microorganisms were deposited with the American Type Culture Collection (ATCC), 12301 Parklawn Drive, Rockville Md. on Apr. 12 1993, and have been assigned the indicated accession number:

| Microorganisms | Accession Number |
| --- | --- |
| E.coli pCBD-ProA1/2097 | 69283 |
| E.coli pET-CBD/BL21 (DE3) | 69282 |
| E.coli pCBD-ProtA1 | 75443 |
| E.coli pET-CBD | 75444.-- |

What is claimed is:

1. An isolated nucleic acid encoding a cellulose binding domain (CBD) comprising the nucleic acid sequence depicted in SEQ ID NO: 1 or its complement.

2. An isolated nucleic acid encoding a cellulose binding domain consisting of the nucleic acid sequence depicted in SEQ ID NO: 1 or its complement.

3. An isolated nucleic acid comprising nucleic acid encoding the cellulose binding domain (CBD) depicted in SEQ ID NO: 2 or said nucleic acid complement.

4. An isolated RNA polynucleotide transcribed from a nucleic acid selected from the group consisting of SEQ ID NO: 1, the complement of SEQ ID NO: 1, SEQ ID NO: 2, and the complement of SEQ ID NO 2.

5. A recombinant vector comprising the nucleic acid of claim 1, claim 3 or claim 2.

6. A host cell transfected with a recombinant vector of claim 5.

7. The host cell of claim 6 which is a bacterial host cell.

8. The host cell of claim 6 which is a mammalian host cell.

9. Plasmid pET-CBD as deposited with the ATCC and assigned ATCC accession number 75444.

10. Recombinant *E. coli* pET-CBD/BL21 (DE3) as deposited with the ATCC and assigned ATCC accession number 69282.

11. A pair of primers capable of priming cDNA synthesis in a polymerase chain reaction, in which each primer is derived from the isolated nucleic acid of claim 1 or 3, wherein one of said primers hybridizes to the sense strand of the nucleic acid, and the other of said primers hybridizes to the complementary strand.

* * * * *